(12) United States Patent
Horikawa

(10) Patent No.: US 10,115,878 B2
(45) Date of Patent: Oct. 30, 2018

(54) OPTICAL SENSOR

(71) Applicant: Shinko Electric Industries Co., Ltd., Nagano-Ken (JP)

(72) Inventor: Yasuyoshi Horikawa, Nagano (JP)

(73) Assignee: Shinko Electric Industries Co., LTD., Nagano-Ken (JP)

( * ) Notice: Subject to any disclaimer, the term of this patent is extended or adjusted under 35 U.S.C. 154(b) by 22 days.

(21) Appl. No.: 15/614,514

(22) Filed: Jun. 5, 2017

(65) Prior Publication Data

US 2017/0358723 A1 Dec. 14, 2017

(30) Foreign Application Priority Data

Jun. 8, 2016 (JP) .................. 2016-114376

(51) Int. Cl.

| | |
|---|---|
| *H01L 33/62* | (2010.01) |
| *H01L 33/20* | (2010.01) |
| *H01L 33/36* | (2010.01) |
| *H01L 33/56* | (2010.01) |
| *A61B 5/024* | (2006.01) |
| *A61B 5/1455* | (2006.01) |
| *A61B 5/02* | (2006.01) |
| *A61B 5/00* | (2006.01) |

(52) U.S. Cl.
CPC .......... *H01L 33/62* (2013.01); *A61B 5/02416* (2013.01); *A61B 5/14552* (2013.01); *H01L 33/20* (2013.01); *H01L 33/36* (2013.01); *H01L 33/56* (2013.01); *A61B 5/02* (2013.01); *A61B 5/02427* (2013.01); *A61B 5/6801* (2013.01); *A61B 2562/046* (2013.01); *A61B 2562/12* (2013.01); *H01L 2224/42* (2013.01); *H01L 2224/48091* (2013.01)

(58) Field of Classification Search
CPC ....................................... H01L 33/62
USPC ....................................... 359/692
See application file for complete search history.

(56) References Cited

U.S. PATENT DOCUMENTS

| | | | |
|---|---|---|---|
| 2010/0125214 A1 | 5/2010 | Brown et al. | |
| 2011/0054583 A1 | 3/2011 | Litt et al. | |
| 2013/0245394 A1 | 9/2013 | Brown et al. | |

(Continued)

FOREIGN PATENT DOCUMENTS

| | | |
|---|---|---|
| JP | 2011-513038 A | 4/2011 |
| JP | 2012-508631 A | 4/2012 |

*Primary Examiner* — James Jones
(74) *Attorney, Agent, or Firm* — Wolf, Greenfield & Sacks, P.C.

(57) ABSTRACT

An optical sensor includes a flexible substrate, a light emitting element, and a light receiving element. The light emitting element and the light receiving element are mounted on element mounting portions and connected to element connection portions by wires. The optical sensor also includes through wirings extending through the substrate. Each through wiring is bonded to the element mounting portion or the element connection portion. The through wirings include a heat radiation through wiring that is located immediately below the light emitting element and bonded to the element mounting portion on which the light emitting element is mounted. The optical sensor further includes light shielding materials and encapsulation resins for surrounding and encapsulating the light emitting element and the light receiving element, respectively.

7 Claims, 14 Drawing Sheets

(56) References Cited

U.S. PATENT DOCUMENTS

| | | | |
|---|---|---|---|
| 2014/0268574 A1* | 9/2014 | Itoi | H01L 23/5389 361/712 |
| 2015/0305625 A1 | 10/2015 | Litt et al. | |
| 2017/0071491 A1 | 3/2017 | Litt et al. | |

* cited by examiner

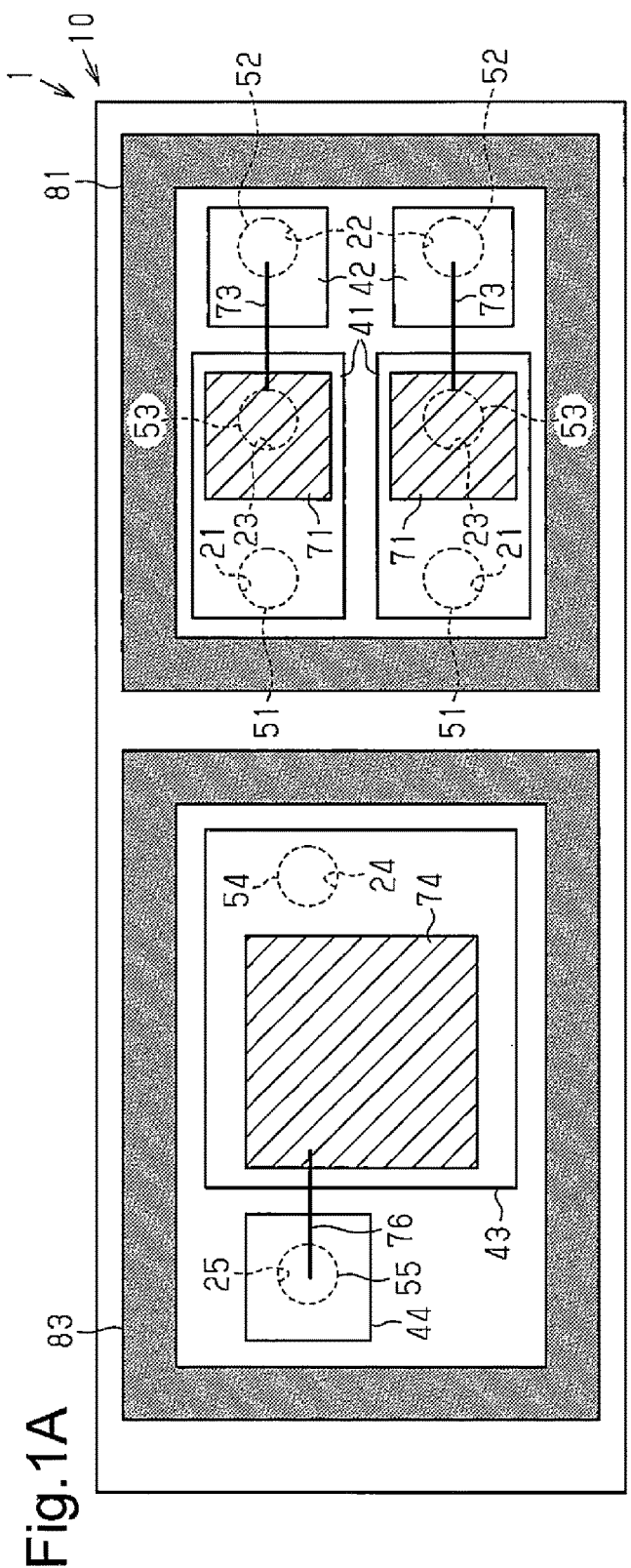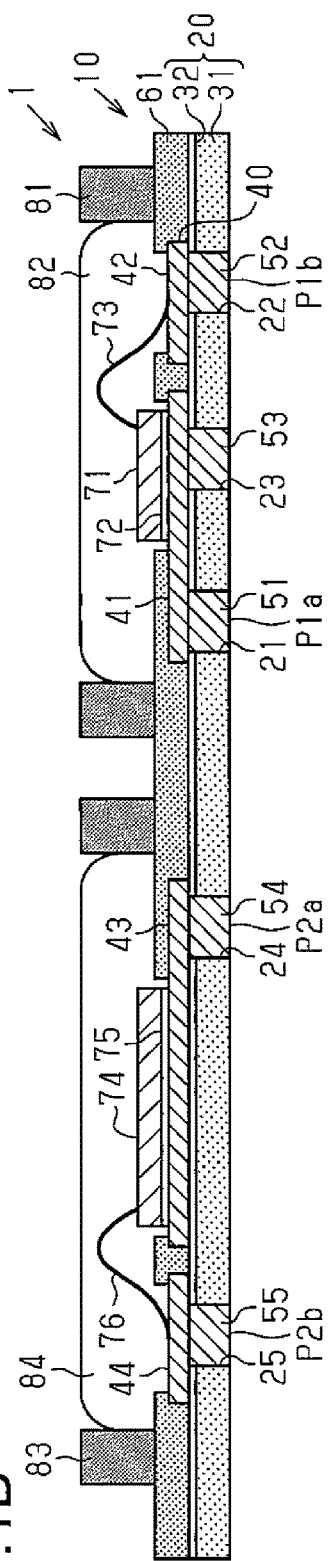
Fig.1A
Fig.1B

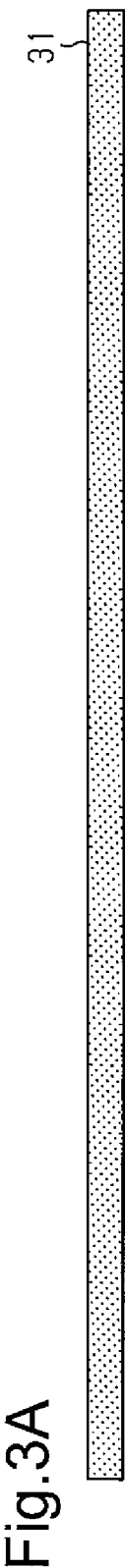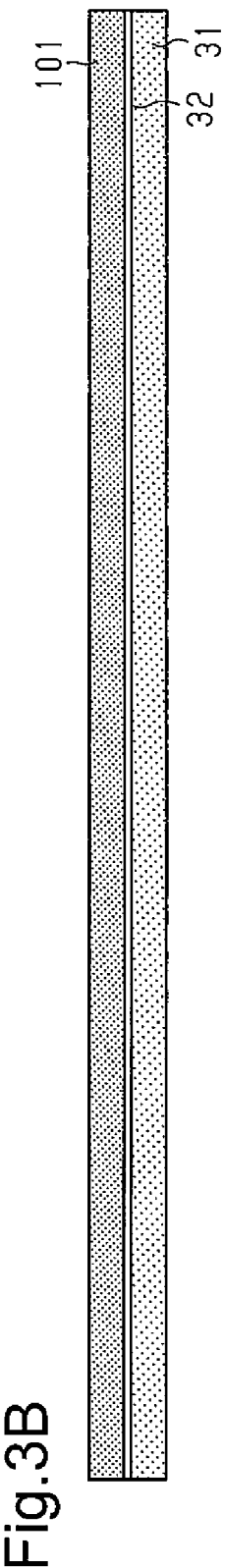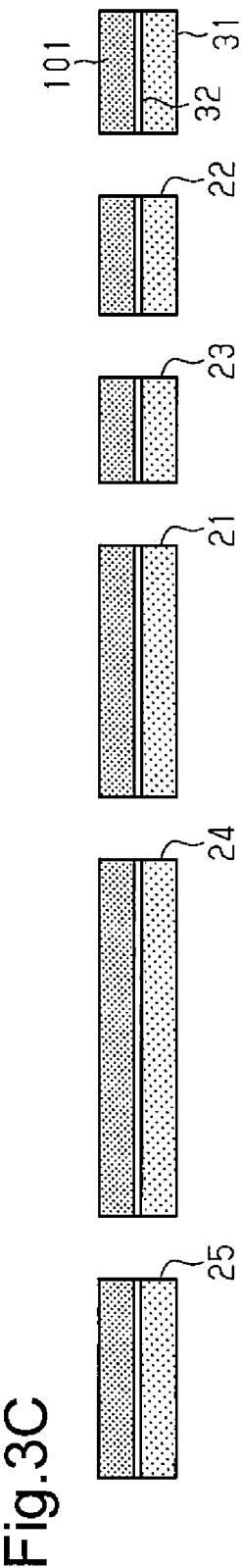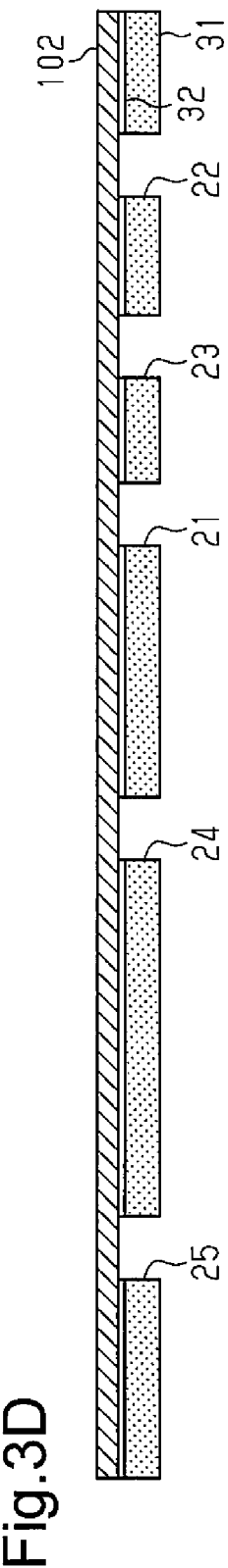

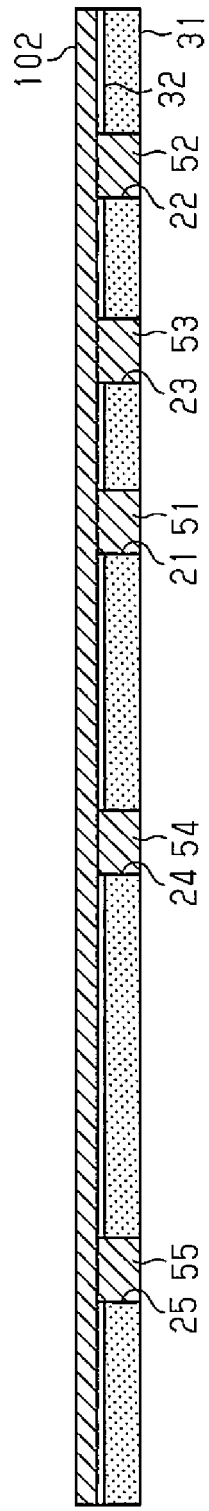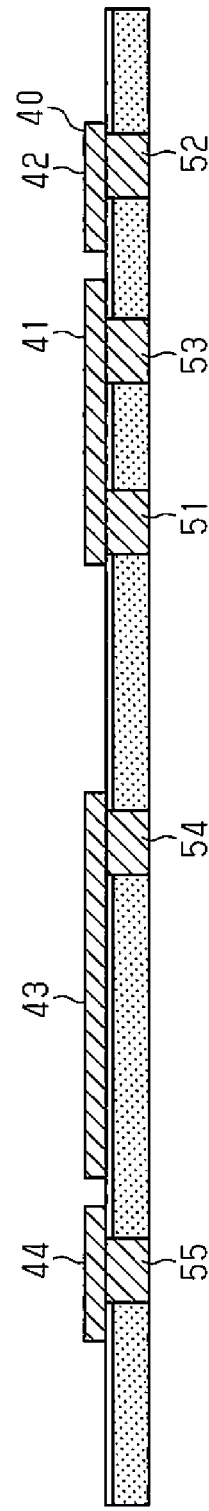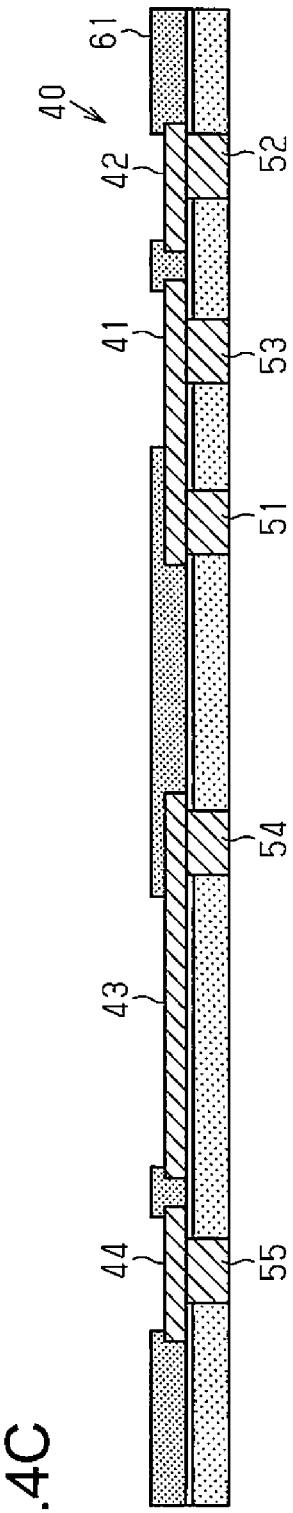

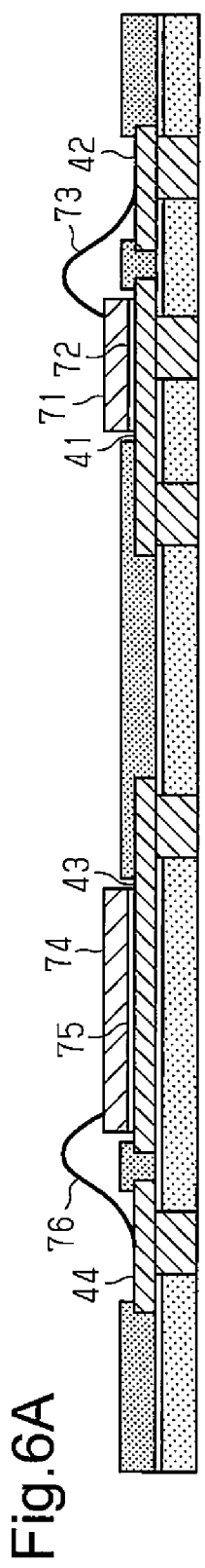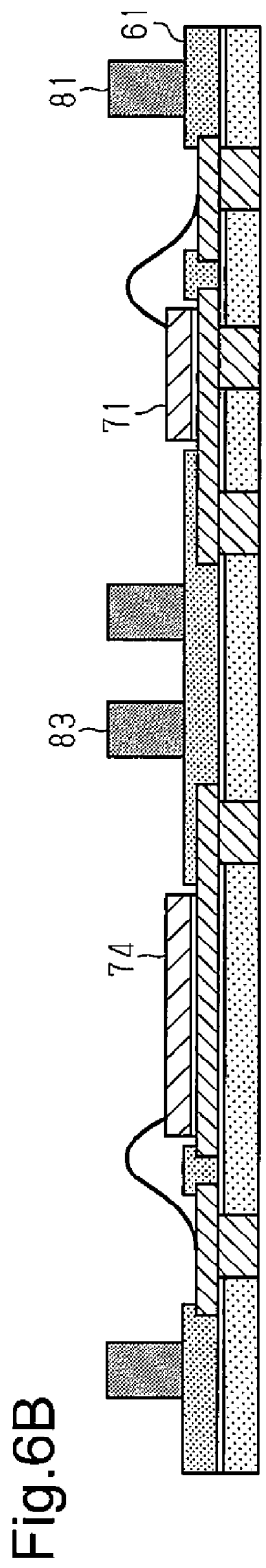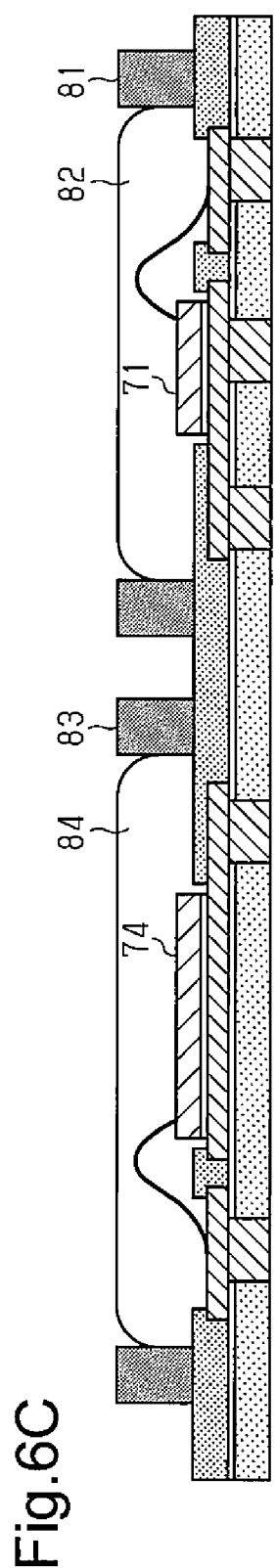

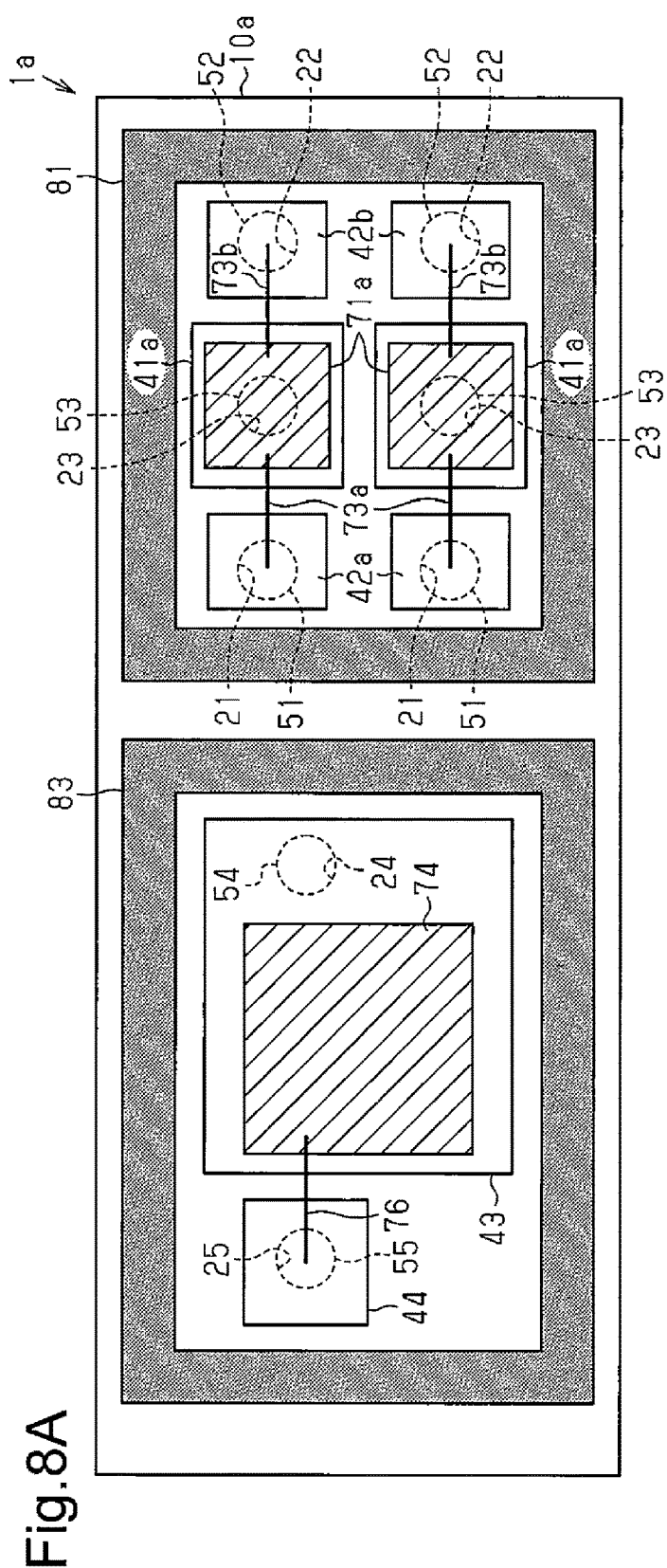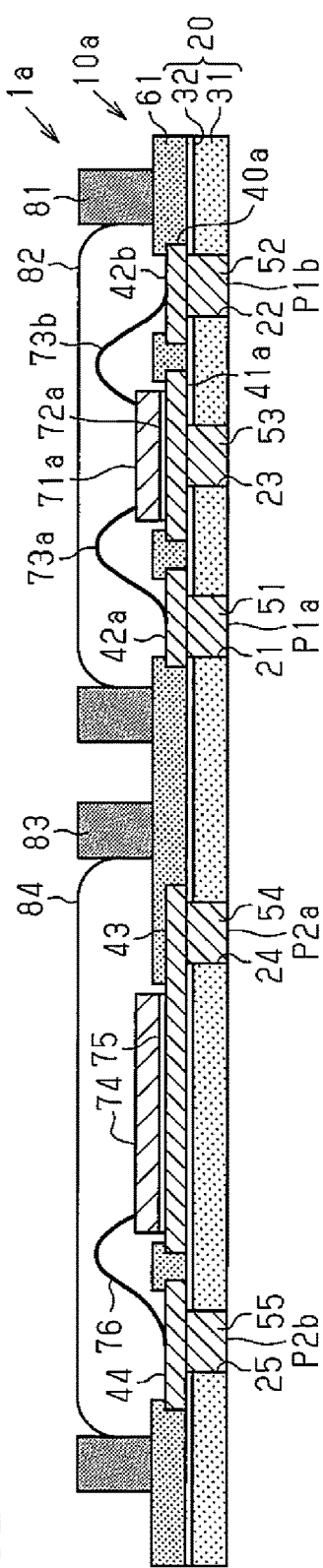

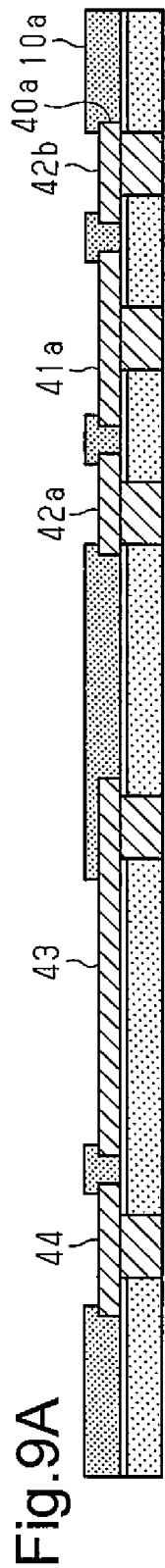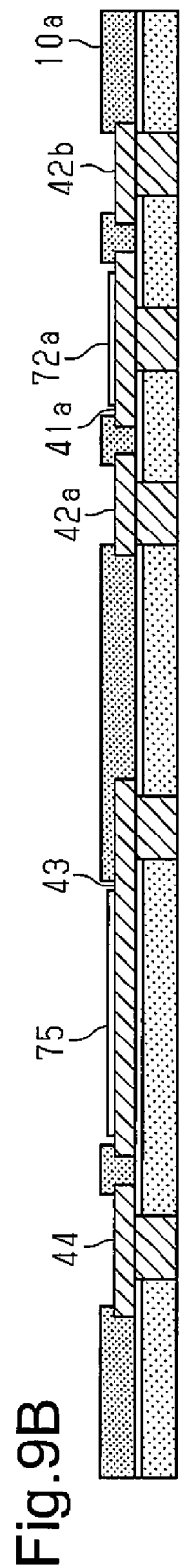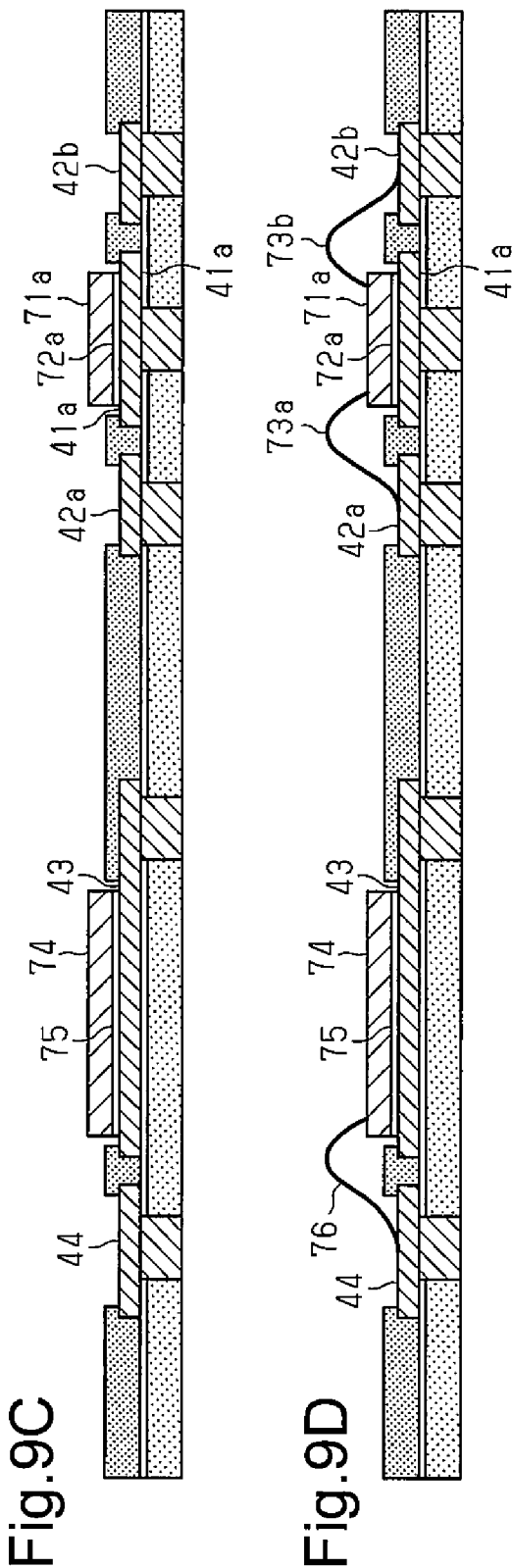

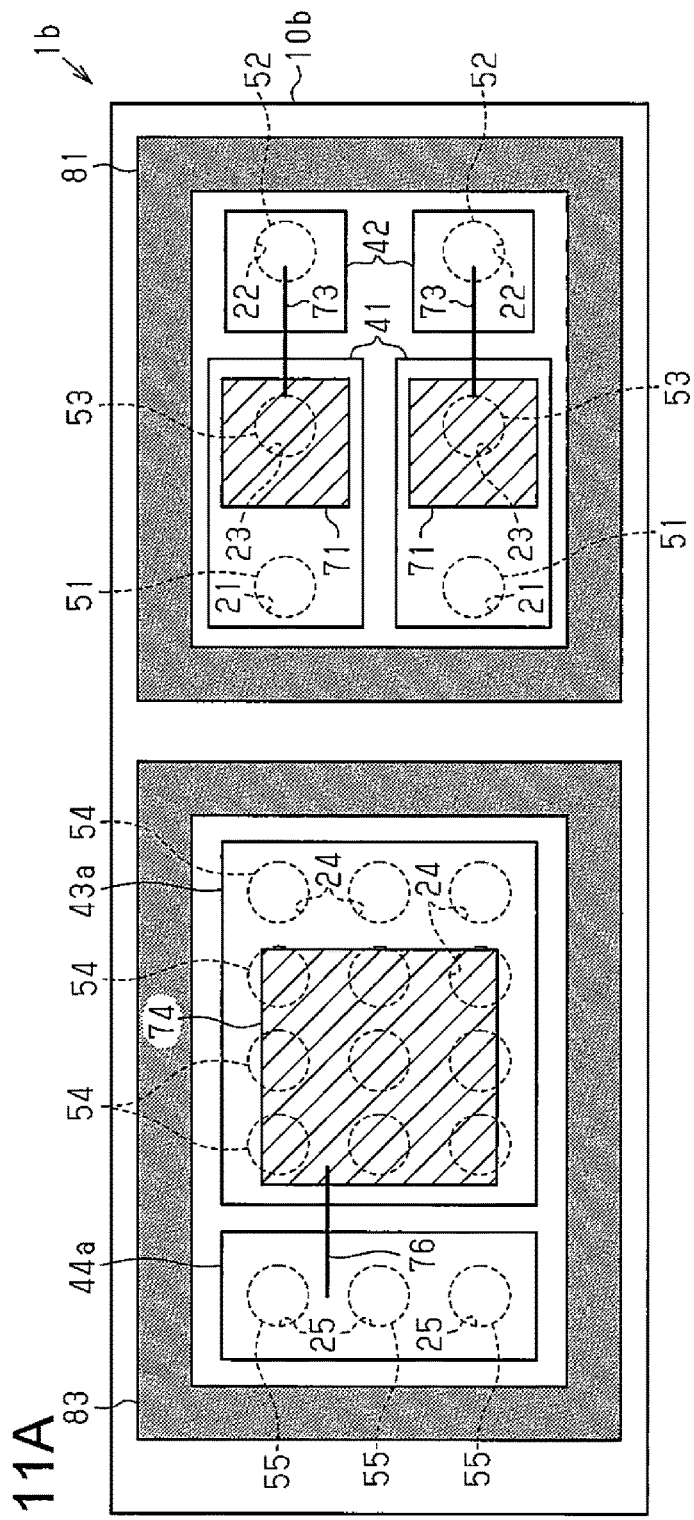
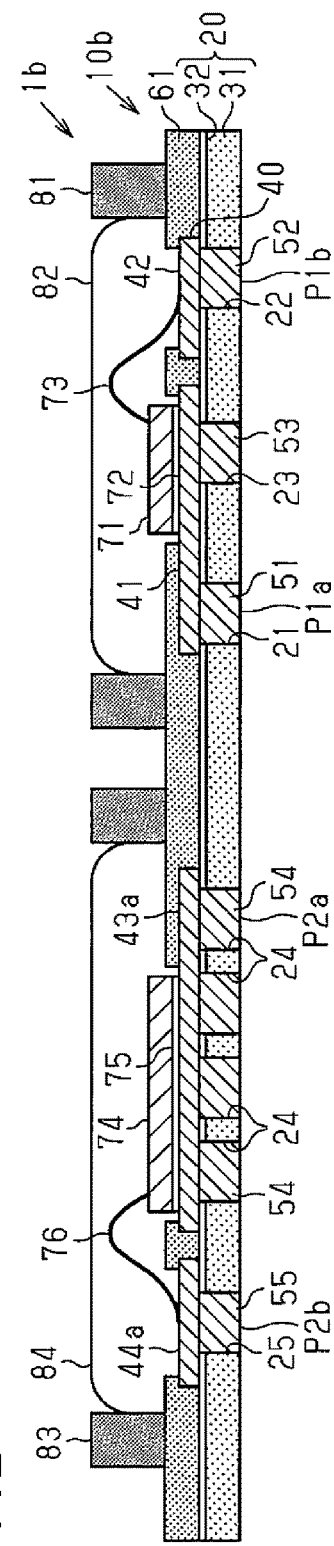
Fig.11A
Fig.11B

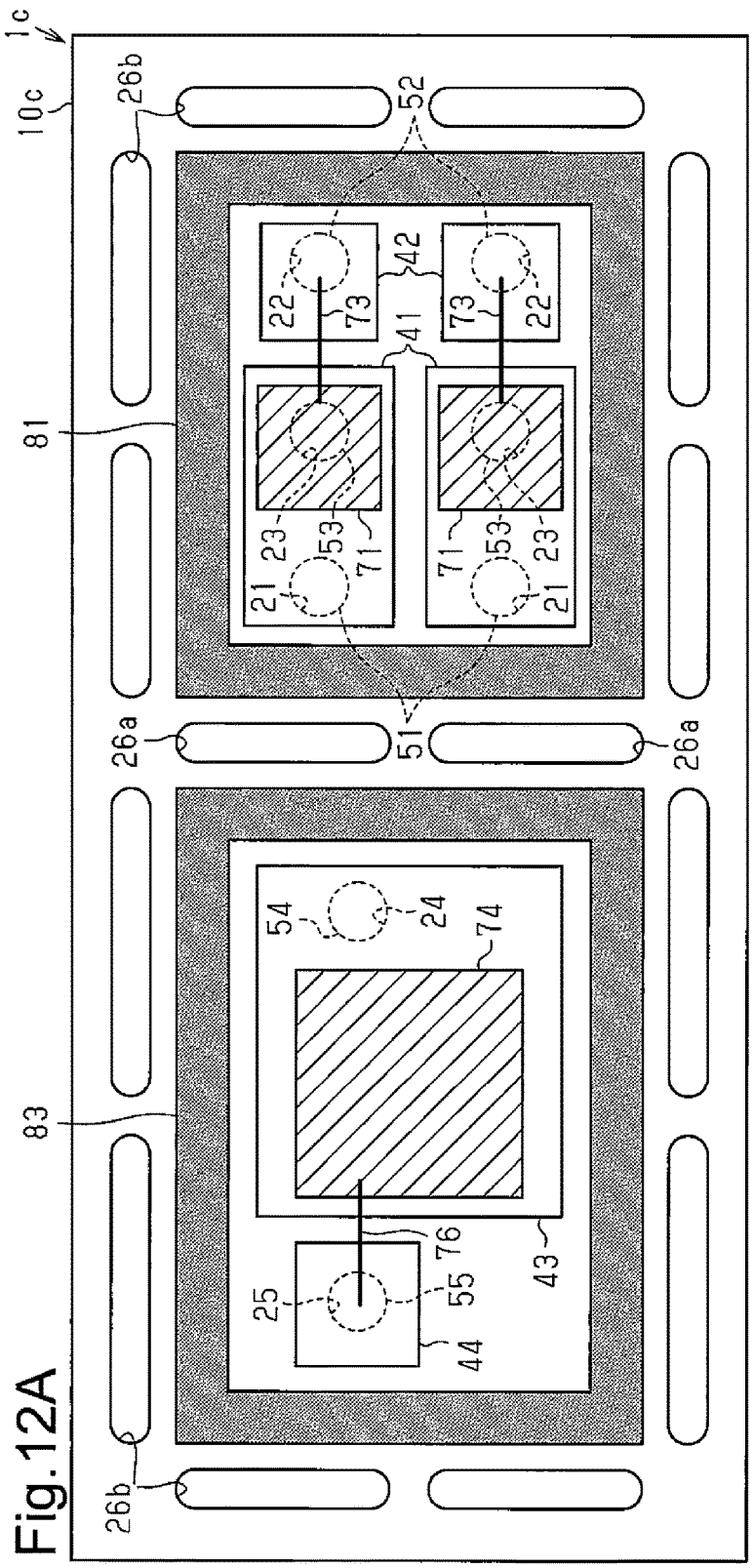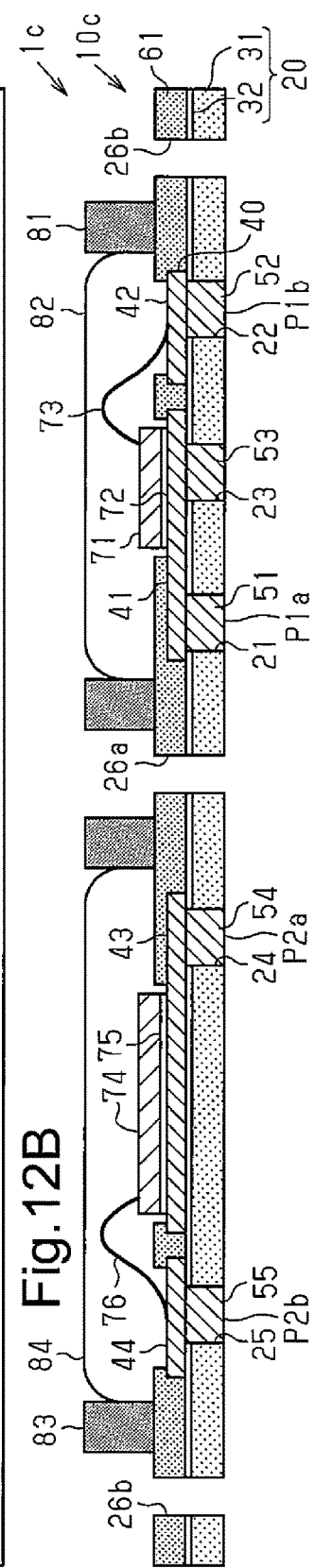
Fig.12A
Fig.12B

US 10,115,878 B2

OPTICAL SENSOR

CROSS-REFERENCE TO RELATED APPLICATIONS

This application is based upon and claims the benefit of priority from prior Japanese Patent Application No. 2016-114376, filed on Jun. 8, 2016, the entire contents of which are incorporated herein by reference.

FIELD

This disclosure relates to an optical sensor and a method for manufacturing an optical sensor.

BACKGROUND

Conventionally, an optical sensor that includes a light emitting element and a light receiving element is used to measure various physical quantities based on the output signal of the light receiving element. Japanese National Phase Laid-Open Patent Publications No. 2012-508631 and No. 2011-513038 describe using optical sensors to obtain biological signals for measuring a local blood oxygen concentration (arterial blood oxygen saturation: $SpO_2$), a pulse wave (PPG), or the like.

SUMMARY

An optical sensor used to obtain biological signals may be placed on a measured object, which includes a flexible part or a curved part, such as a human body surface. It is necessary to bring the optical sensor into close contact with the measured object.

One embodiment is an optical sensor. The optical sensor includes a flexible substrate, a light emitting element, and a light receiving element. The optical sensor also includes a plurality of element mounting portions formed on an upper surface of the substrate. Each of the light emitting element and the light receiving element is mounted on one of the element mounting portions. The optical sensor also includes a plurality of element connection portions formed on the upper surface of the substrate. Each of the element connection portions is connected to one of the light emitting element and the light receiving element by a wire. The optical sensor also includes a plurality of through wirings respectively formed in a plurality of through holes extending through the substrate. Each of the through wirings is bonded to one of the element mounting portions or one of the element connection portions. The through wirings include a heat radiation through wiring that is located immediately below the light emitting element and bonded to the element mounting portion on which the light emitting element is mounted. The optical sensor also includes a plurality of light shielding materials that are each frame-shaped. Each of the light emitting element and the light receiving element is surrounded by one of the light shielding materials. The optical sensor further includes a plurality of encapsulation resins each arranged within a region surrounded by one of the light shielding materials. Each of the light emitting element and the light receiving element is encapsulated by one of the encapsulation resins.

Another embodiment is a method for manufacturing an optical sensor. The method includes forming a plurality of through holes in a flexible substrate, arranging a metal layer on an upper surface of the substrate to cover the through holes, and forming a plurality of through wirings in the through holes. The method also includes patterning the metal layer to form a plurality of element mounting portions and a plurality of element connection portions. The method also includes mounting a light emitting element and a light receiving element on the element mounting portions. The method also includes connecting the light emitting element and the light receiving element to the element connection portions by wires, respectively. The method also includes forming a plurality of light shielding materials to respectively surround the light emitting element and the light receiving element. The method further includes forming a plurality of encapsulation resins to respectively encapsulate the light emitting element and the light receiving element. The through wirings include a heat radiation through wiring that is formed immediately below the light emitting element and bonded to the element mounting portion on which the light emitting element is mounted.

Other embodiments and advantages thereof will become apparent from the following description, taken in conjunction with the accompanying drawings, illustrating by way of example the principles of the invention.

It is to be understood that both the foregoing general description and the following detailed description are exemplary and explanatory and are not restrictive of the invention, as claimed.

BRIEF DESCRIPTION OF THE DRAWINGS

The embodiments, together with objects and advantages thereof, may best be understood by reference to the following description of the presently preferred embodiments together with the accompanying drawings in which:

FIG. 1A is a schematic plan view illustrating a first embodiment of an optical sensor;

FIG. 1B is a schematic cross-sectional view of the optical sensor illustrated in FIG. 1A;

FIGS. 3A to 3D, 4A to 4C, 5A to 5C, 6A to 6C, and 7A to 7E are schematic cross-sectional views illustrating a method for manufacturing the optical sensor illustrated in FIG. 1B;

FIG. 8A is a schematic plan view illustrating a second embodiment of an optical sensor;

FIG. 8B is a schematic cross-sectional view of the optical sensor illustrated in FIG. 8A;

FIGS. 9A to 9D and 10A to 10C are schematic cross-sectional views illustrating a method for manufacturing the optical sensor illustrated in FIG. 8B;

FIG. 11A is a schematic plan view illustrating a third embodiment of an optical sensor;

FIG. 11B is a schematic cross-sectional view of the optical sensor illustrated in FIG. 11A;

FIG. 12A is a schematic plan view illustrating a fourth embodiment of an optical sensor;

FIG. 12B is a schematic cross-sectional view of the optical sensor illustrated in FIG. 12A;

DESCRIPTION OF THE EMBODIMENTS

Figure 2:
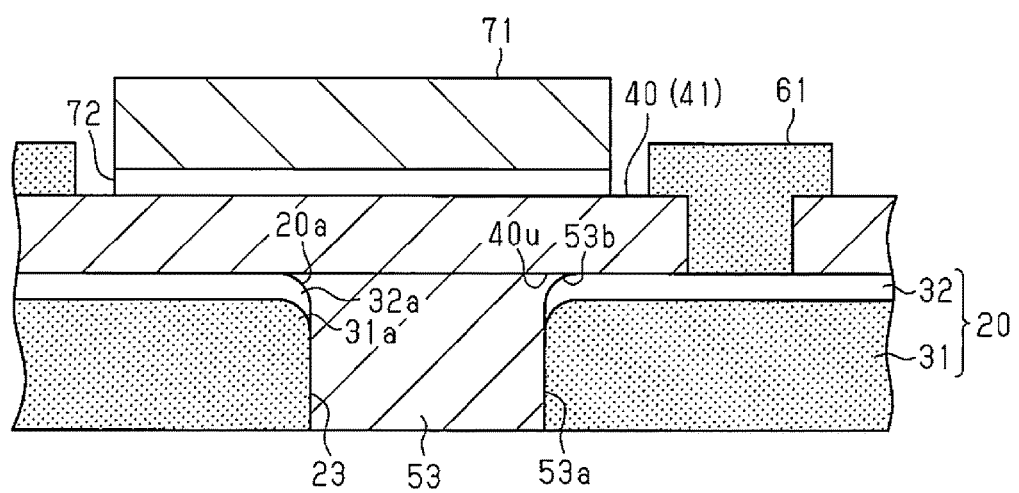
FIG. 2 is a partially enlarged cross-sectional view of the optical sensor illustrated in FIG. 1B.

Embodiments will now be described with reference to the accompanying drawings. Elements in the drawings may be partially enlarged for simplicity and clarity and thus have not necessarily been drawn to scale. To facilitate understanding, hatching lines may not be illustrated or be replaced by shadings in the cross-sectional drawings.

First Embodiment

An optical sensor 1 according to a first embodiment will now be described. As illustrated in FIGS. 1A and 1B, the optical sensor 1 includes a wiring substrate 10, light emitting elements 71, and a light receiving element 74. The light emitting elements 71 and the light receiving element 74 are mounted on the wiring substrate 10.

The wiring substrate 10 includes a flexible substrate 20, a wiring layer 40, and a protective film 61. The wiring layer 40 and the protective film 61 are formed on one of the upper and lower surfaces of the substrate 20 (upper surface in FIG. 1A). The substrate 20 includes a base material 31 and an adhesive layer 32 formed on the upper surface of the base material 31.

The base material 31 is flexible and, for example, rectangular in a plan view. For example, a flexible film substrate using a resin, such as a polyimide or a polyester resin, or a liquid crystal polymer, or the like may be used as the base material 31. The base material 31 may have a thickness of, for example, 25 to 100 micrometer (μm). The adhesive layer 32 is formed on the upper surface of the base material 31 to adhere the wiring layer 40 to the base material 31. For example, an epoxy, polyimide, or silicone adhesive may be used as the material of the adhesive layer 32.

The wiring layer 40 includes element mounting portions 41 and element connection portions 42. The light emitting elements 71 are, respectively, mounted on the element mounting portions 41 and connected to the element connection portions 42. Further, the wiring layer 40 includes an element mounting portion 43 and an element connection portion 44. The light receiving element 74 is mounted on the element mounting portion 43 and connected to the element connection portion 44. For example, copper (Cu) or a copper alloy may be used as the material of the wiring layer 40.

As illustrated in FIG. 1A, in the first embodiment, two light emitting elements 71 are mounted on the wiring substrate 10. The wiring substrate 10 includes two element mounting portions 41 and two element connection portions 42 in correspondence with the two light emitting elements 71. For example, the two light emitting elements 71 each emit light having a different frequency. The light receiving element 74 has light receiving characteristics according to the light emitted from the two light emitting elements 71. Each of the light emitting elements 71 may emit light having the same frequency.

As illustrated in FIG. 1B, the protective film 61 covers the upper surface of the adhesive layer 32. Further, the protective film 61 covers portions of the wiring layer 40 (portions of the element mounting portions 41, 43 and portions of the element connection portions 42, 44). The protective film 61 includes openings that partially expose the upper surfaces of the element mounting portions 41, 43 and the upper surfaces of the element connection portions 42, 44. A surface-processed layer (not illustrated) is formed on each of the exposed upper surfaces of the element mounting portions 41, 43 and the element connection portions 42, 44. Examples of the surface-processed layer include a gold (Au) layer, a nickel (Ni) layer/Au layer (metal layer in which Ni layer is bottom layer and Au layer is formed on Ni layer), an Ni layer/palladium (Pd) layer/Au layer (metal layer in which Ni layer, Pd layer, and Au layer are stacked in this order, with Ni layer serving as the bottom layer). Alternatively, the surface-processed layer may be formed by performing an anti-oxidation process such as an Organic Solderability Preservative (OSP) process on the upper surface of the wiring layer 40. When performing, for example, the OSP process, an organic coating such as that of an azole compound or an imidazole compound is formed as the surface-processed layer on the surface of the wiring layer 40.

Through holes 21, 22 extending through the base material 31 and the adhesive layer 32 are formed in the substrate 20. The through holes 21 partially expose the lower surfaces of the element mounting portions 41 and the through holes 22 partially expose the lower surfaces of the element connection portions 42. As illustrated in FIG. 1A, the through holes 21 are arranged at locations that are not overlapped with the light emitting elements 71 mounted on the element mounting portions 41 in a plan view.

Through wirings 51, 52 are formed in the through holes 21, 22. The through wirings 51 are bonded to the element mounting portions 41 and the through wirings 52 are bonded to the element connection portions 42. Each of the through wirings 51, 52 includes a lower end face that is exposed at the lower surface of the substrate 20. The exposed lower end face of each through wiring 51 functions as an external connection terminal P1a and the exposed lower end face of each through wiring 52 functions as an external connection terminal P1b. For example, copper or a copper alloy may be used as the material of the through wirings 51, 52. The through wirings 51, 52 may be, for example, a plating metal (e.g., copper plating) formed in the through holes 21, 22 or a conductive paste (e.g., copper paste) with which the through holes 21, 22 are filled.

A surface-processed layer may be formed on the exposed lower end faces (external connection terminals P1a, P1b) of the through wirings 51, 52. For example, Au or an Au alloy, Ni or an Ni alloy, or Pd or a Pd alloy is used as the material of the surface-processed layer. Examples of the surface-processed layer include an Au layer, an Ni layer/Au layer, and an Ni layer/Pd layer/Au layer. Alternatively, the surface-processed layer may be formed by performing an anti-oxidation process such as an OSP process on the exposed lower end faces of the through wirings 51, 52. When the surface-processed layer is formed on the exposed lower end faces of the through wirings 51, 52, the surface-processed layer functions as external connection terminals.

Through holes 23 extending through the base material 31 and the adhesive layer 32 are also formed in the substrate 20. The through holes 23 are located immediately below the light emitting elements 71. The through holes 23 partially expose the lower surfaces of the element mounting portions 41 at locations where the light emitting elements 71 are mounted. That is, as illustrated in FIG. 1A, the through holes 23 are arranged at locations overlapped with the light emitting elements 71 in a plan view.

Through wirings 53 are formed in the through holes 23. The through wirings 53 are bonded to the element mounting portions 41. Each of the through wirings 53 includes a lower end face that is exposed at the lower surface of the substrate 20. The heat generated by each light emitting element 71 is transmitted through the corresponding element mounting portion 41 to the corresponding through wiring 53 located immediately below the light emitting element 71. The heat transmitted to the through wirings 53 is then released from the exposed lower end faces of the through wirings 53. Thus, the exposed lower end faces of the through wirings 53 function as heat radiation surfaces that release the heat generated by the light emitting elements 71 mounted on the element mounting portions 41. That is, each of the through wirings 53 functions as a heat conductive member (heat radiation through wiring: thermal via) that releases the heat generated by the light emitting elements 71. For example, copper or a copper alloy may be used as the material of the heat radiation through wirings 53. In the same manner as the through wirings 51, 52, a surface-processed layer may be formed on the exposed lower end faces of the heat radiation through wirings 53.

Through holes 24, 25 extending through the base material 31 and the adhesive layer 32 are also formed in the substrate 20. The through hole 24 partially exposes the lower surface of the element mounting portion 43 and the through hole 25 partially exposes the lower surface of the element connection portion 44. As illustrated in FIG. 1A, the through hole 24 is arranged at a location that is not overlapped with the light receiving element 74 mounted on the element mounting portion 43 in a plan view.

Through wirings 54, 55 are formed in the through holes 24, 25. The through wiring 54 is bonded to the element mounting portion 43 and the through wiring 55 is bonded to the element connection portion 44. Each of the through wirings 54, 55 includes a lower end face that is exposed at the lower surface of the substrate 20. The exposed lower end face of the through wiring 54 functions as an external connection terminal $p2a$ and the exposed lower end face of the through wiring 55 functions as an external connection terminal $P2b$. For example, copper or a copper alloy may be used as the material of the through wirings 54, 55. In the same manner as the through wirings 51, 52, a surface-processed layer may be formed on the exposed lower end faces of the through wirings 54, 55.

The light emitting elements 71 are connected to the upper surfaces of the element mounting portions 41 by connection members 72. In the first embodiment, each of the light emitting elements 71 includes electrodes that are arranged on the upper and lower surfaces of the light emitting element 71. As the connection members 72, an electrically conductive adhesive, for example, a silver paste may be used. The electrode arranged on the lower surface of each light emitting element 71 is connected to the corresponding element mounting portion 41 by the corresponding connection member 72. The electrode arranged on the upper surface of each light emitting element 71 is connected to the corresponding element connection portion 42 by a wire 73. As the wire 73, for example, an Au wire may be used.

The light receiving element 74 is connected to the upper surface of the element mounting portion 43 by a connection member 75. In the first embodiment, the light receiving element 74 includes electrodes that are arranged on the upper and lower surfaces of the light receiving element 74. As the connection member 75, an electrically conductive adhesive, for example, a silver paste may be used. The electrode arranged on the lower surface of the light receiving element 74 is connected to the element mounting portion 43 by the connection member 75. The electrode arranged on the upper surface of the light receiving element 74 is connected to the element connection portion 44 by a wire 76. As the wire 76, for example, an Au wire may be used.

Light shielding materials 81, 83 are arranged on the wiring substrate 10. The light shielding materials 81, 83 are fixed to the upper surface of the protective film 61 of the wiring substrate 10.

The light shielding material 81 is formed to have the shape of a rectangular frame and surrounds the light emitting elements 71. An insulative resin that is colored with, for example, black may be used as the light shielding material 81. As the insulative resin, for example, an insulative resin, such as an epoxy resin or a polyimide resin, or a resin material in which filler such as silica or alumina is mixed into such an insulative resin may be used. Alternatively, the insulative resin may be, for example, an opaque black resist obtained by mixing a photosensitive material in an opaque black resin. A black pigment of carbon black, titanium black, or the like, or a mixture of multiple types of pigments may be used as a colorant mixed into the insulative resin.

An encapsulation resin 82 is formed within a region surrounded by the light shielding material 81 to encapsulate the light emitting elements 71. The encapsulation resin 82 is light transmissive and transmits light according to the light emitting characteristics of the light emitting elements 71. As the encapsulation resin 82, for example, a silicone resin may be used.

The light shielding material 83 is formed to have the shape of a rectangular frame and surrounds the light receiving element 74. The same material as the light shielding material 81 may be used as the light shielding material 83. An encapsulation resin 84 is formed within a region surrounded by the light shielding material 83 to encapsulate the light receiving element 74. The encapsulation resin 84 is light transmissive and transmits light according to the light receiving characteristics of the light receiving element 74. As the encapsulation resin 84, for example, a silicone resin may be used.

As illustrated in FIG. 2, each of the through holes 23 (only one illustrated in FIG. 1) extends through the base material 31 and the adhesive layer 32 of the substrate 20. The heat radiation through wiring 53 is formed in the through hole 23. The through hole 23 may be, for example, circular in a plan view.

The through hole 23 is formed by performing a stamping process using a mold or the like to the based material 31 and the adhesive layer 32 from an upper surface side of the substrate 20, that is, from the adhesive layer 32. Therefore, as illustrated in FIG. 2, the upper edges of walls of the base material 31 and the adhesive layer 32, which are in contact with a side surface 53*a* of the heat radiation through wiring 53, are deformed through the stamping process to sag downwardly.

Thus, the base material 31 includes a curved and rounded edge 31*a*, that is, "sag" extending in the stamping direction, in the upper surface of the base material 31 at an upper end portion of each through hole 23. Also, the adhesive layer 32 includes a curved and rounded edge 32*a* in the upper surface of the adhesive layer 32 at the upper end portion of each through hole 23. Thus, the substrate 20 includes a curved and rounded edge 20*a* in the upper surface of the substrate 20 at the upper end portion of each through hole 23. The upper end portion of the through hole 23 defined by the rounded edge 20*a* of the substrate 20 is covered by the wiring layer 40 (element mounting portion 41). Thus, the through wiring 53 includes a flange 53*b* that is formed between the rounded edge 20*a* of the substrate 20 and the wiring layer 40 (element mounting portion 41). The flange 53*b* is formed such that the diameter increases along the rounded edge 20*a* of the substrate 20 from the side surface 53*a* of the through wiring 53. Thus, the diameter of the flange 53*b* is larger than the diameter of the through hole 23.

The wiring layer 40 is formed by a metal foil (e.g., copper foil) adhered to the upper surface of the substrate 20, that is, the upper surface of the base material 31 by the adhesive layer 32. Thus, the wiring layer 40 is arranged on the upper surface of the substrate 20 to close the upper side (i.e., upper end portion) of the through hole 23. The through wiring 53 is formed in the through hole 23 of the substrate 20 by performing a given process (e.g., plating process or paste filling process) from the lower surface of the substrate 20. Thus, the gap between the edge 20a of the substrate 20 (edge 32a of adhesive layer 32) and a lower surface 40u of the wiring layer 40 (element mounting portion 41) is filled with the flange 53b of the through wiring 53. The flange 53b limits the separation of the heat radiation through wiring 53 from the through hole 23 of the substrate 20.

When the through wirings 53 are formed through electrolytic plating, the upper end portions of the through wiring 53 are bonded to the wiring layer 40 (element mounting portions 41). In contrast, the side surface 53a of each through wiring 53 is only in contact with the inner surface of the through hole 23. Thus, when a force such as bending is applied to the substrate 20, the stress in the substrate 20 (base material 31 and adhesive layer 32) is hard to be transmitted to the side surface 53a of the through wiring 53.

The through holes 21, 22, 24, 25 illustrated in FIG. 1B are formed in the same manner as the through holes 23 illustrated in FIG. 2. Although not illustrated in details in FIG. 1B, the substrate 20 includes curved and rounded edges at the upper end portions of the through holes 21, 22, 24, 25 covered by the wiring layer 40 (element mounting portions 41, element connection portions 42, element mounting portion 43, and element connection portion 44). Then, the through wirings 51, 52, 54, 55 illustrated in FIG. 1B are formed in the same manner as the heat radiation through wirings 53 described above. Therefore, like the heat radiation through wirings 53, the flanges of the through wirings 51, 52, 54, 55 limit the separation of the through wirings 51, 52, 54, 55 from the through holes 21, 22, 24, 25, respectively. Further, the stress in the substrate 20 (base material 31 and adhesive layer 32) is hard to be transmitted to the side surfaces of the through wirings 51, 52, 54, 55.

A method for manufacturing the optical sensor 1 will now be described. In the description, reference characters are given to elements as necessary. Reference characters may not be given to elements that are not described. For the sake of brevity, portions that ultimately become elements of the optical sensor 1 are indicated by reference characters used to denote the final elements.

A process for forming the wiring substrate 10 will now be first described.

As illustrated in FIG. 3A, the base material 31 is prepared. An insulative resin film (e.g., polyimide film) having a thickness of 25 µm to 100 µm is used as the base material 31.

As illustrated in FIG. 3B, the adhesive layer 32 and a protective film 101 are formed on the upper surface of the base material 31. The adhesive layer 32 is, for example, an epoxy adhesive. As the material of the protective film 101, a polyethylene terephthalate (PET) film, and the like may be used.

As illustrated in FIG. 3C, the stamping process using a mold is performed from the side of the protective film 101 to form the through holes 21 to 25 extending through the base material 31, the adhesive layer 32, and the protective layer 101.

As illustrated in FIG. 3D, the protective film 101 (refer to FIG. 3C) is removed, and a metal layer 102 is formed on the upper surface of the adhesive layer 32. The metal layer 102 may be formed by, for example, laminating a metal foil (e.g., copper foil) on the upper surface of the adhesive layer 32.

As illustrated in FIG. 4A, electrolytic plating (e.g., electrolytic copper plating) using the metal layer 102 as the plating power supplying layer is performed to form the through wirings 51 to 55 in the through holes 21 to 25. A protective film such as a resist film (not illustrated) covers and protects the upper surface of the metal layer 102 from the plating solution.

As illustrated in FIG. 4B, the metal layer 102 illustrated in FIG. 4A is patterned to form the wiring layer 40. As an example, firstly, an etching mask (not illustrated) including openings at desired positions is formed on the upper surface of the metal layer 102 illustrated in FIG. 4A. As the material of the etching mask, for example, a photosensitive dry film resist or a liquid photoresist (e.g., dry film resist or liquid resist such as novolac resin, acrylic resin, and the like) may be used. For example, the upper surface of the metal layer 102 illustrated in FIG. 4A is laminated with the dry film through thermo-compression. The dry film is patterned through photolithography to obtain the etching mask described above. Next, the metal layer 102 is etched through the openings of the etching mask to form the wiring layer 40 illustrated in FIG. 4B. Then, the etching mask is removed with, for example, an alkaline stripping solution. During the etching process, a protective film such as a resist film (not illustrated) covers the lower surface of the substrate 20 to protect the through wirings 51 to 55 from the etching process.

As illustrated in FIG. 4C, the protective film 61 is formed to cover the upper surface of the adhesive layer 32 and portions of the wiring layer 40. The protective film 61 is obtained by, for example, applying a photosensitive solder resist to the adhesive layer 32 and the wiring layer 40 and patterning the resist through photolithography. If necessary, the surface-processed layer is formed on the surface of the wiring layer 40 (element mounting portions 41, 43 and element connection portions 42, 44) exposed from the protective film 61 and the surfaces of the through wirings 51 to 55 exposed at the lower surface of the substrate 20. The surface-processed layer may be, for example, an Ni layer/Au layer formed through electrolytic plating or electroless plating.

Next, a process for mounting the elements on the wiring substrate 10 will now be described.

Figure 5A:
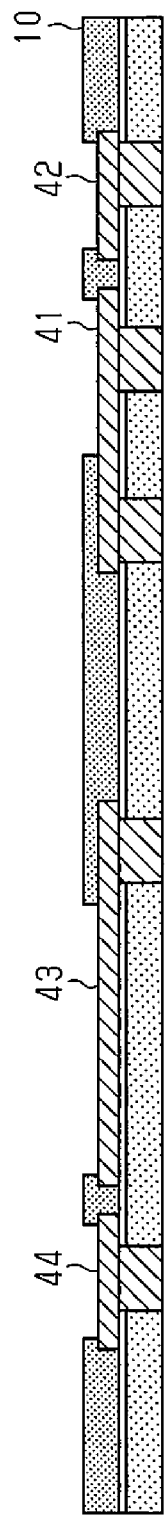

As illustrated in FIG. 5A, the wiring substrate 10 formed by the method described above is prepared.

Figure 5B:
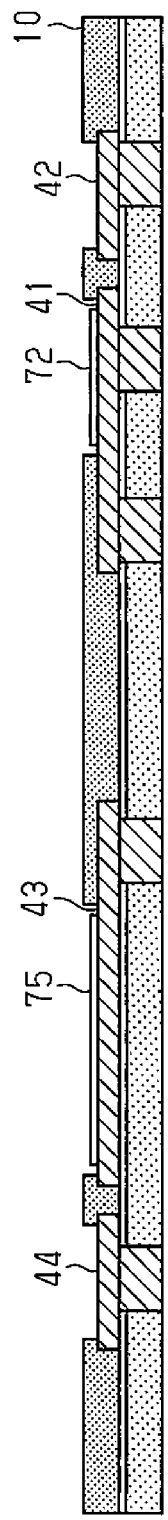

As illustrated in FIG. 5B, the connection members 72, 75 are formed on the upper surfaces of the element mounting portions 41, 43. As the connection members 72, 75, for example, a silver paste may be used. The connection members 72, 75 are applied to the upper surfaces of the element mounting portions 41, 43 by using, for example, a dispenser.

Figure 5C:
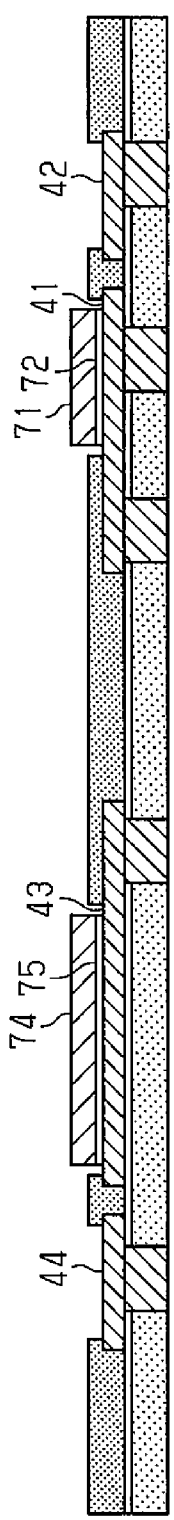

As illustrated in FIG. 5C, the light emitting elements 71 and the light receiving element 74 are mounted on the connection members 72, 75, respectively, and the connection members 72, 75 are cured by, for example, a thermal treatment. In the first embodiment, each of the light emitting elements 71 and the light receiving element 74 includes electrodes arranged on the upper and lower surfaces. Through this step, the light emitting elements 71 are mechanically fixed to and electrically connected to the element mounting portions 41, and the light receiving element 74 is mechanically fixed to and electrically connected to the element mounting portion 43.

As illustrated in FIG. 6A, the light emitting elements 71 are connected to the element connection portions 42 by the wires 73, and the light receiving element 74 is connected to the element connection portion 44 by the wire 76.

As illustrated in FIG. 6B, the light shielding materials 81, 83 are formed. The light shielding materials 81, 83 are obtained by, for example, arranging the light shielding materials 81, 83 using an epoxy resin or the like, which is in a semi-cured state, on the upper surface of the protective layer 61 in a frame-shaped manner and thermally curing the light shielding materials 81, 83.

As illustrated in FIG. 6C, the region surrounded by the light shielding material 81 is filled with the encapsulation resin 82 to encapsulate the light emitting elements 71. Also, the region surrounded by the light shielding material 83 is filled with the encapsulation resin 84 to encapsulate the light emitting element 74.

The forming of the through holes 21 to 25 and the through wirings 51 to 55 will now be described. In the following, the through holes 23 and the through wirings 53 will be described with reference to FIGS. 7A to 7E. The same applies to the through holes 21, 22, 24, 25 and the through holes 51, 52, 54, 55.

Figure 7A:
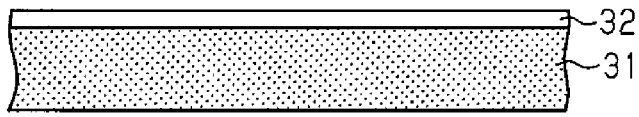

As illustrated in FIG. 7A, the adhesive layer 32 is formed on the upper surface of the base material 31. The protective film 101 illustrated in FIG. 3B is not illustrated in FIG. 7A.

Figure 7B:
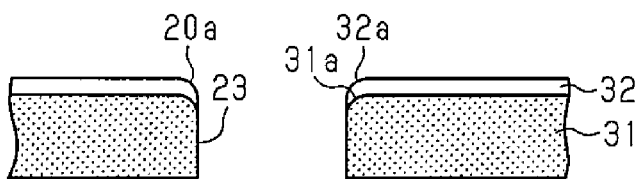

As illustrated in FIG. 7B, the stamping process using a mold is performed from the side of the adhesive layer 32 to form the through holes 23 (only one illustrated in FIG. 7A) extending through the adhesive layer 32 and the base material 31. Through the stamping process, the upper edges of walls of the base material 31 and the adhesive layer 32, which define the through hole 23 and ultimately contact the side surface 53a (refer to FIG. 2) of the through wiring 53, are deformed to sag downwardly. This forms the curved and rounded edge 32a, that is, "sag" extending in the stamping direction, in the upper surface of the adhesive layer 32 at the upper end portion of the through hole 23. Also, the curved and rounded edge 31a is formed in the upper surface of the base material 31.

Figure 7C:
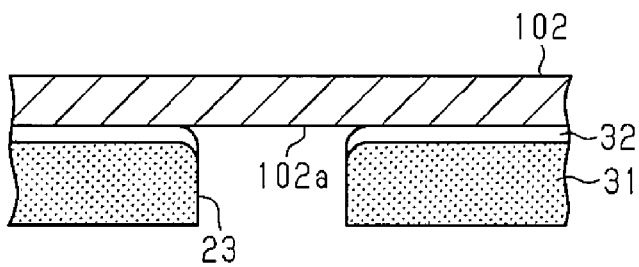

As illustrated in FIG. 7C, the metal layer 102 is formed on the upper surface of the adhesive layer 32. The metal layer 102 may be formed by, for example, laminating a metal foil (e.g., copper foil) on the upper surface of the adhesive layer 32.

Figure 7D:
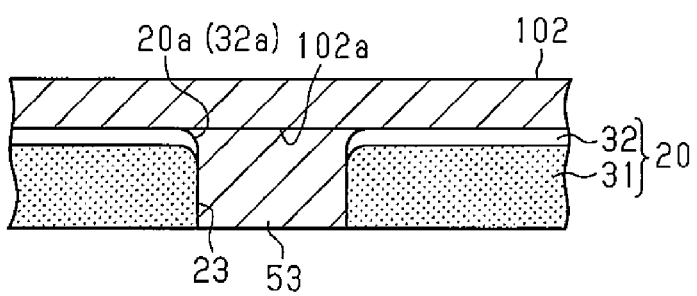

As illustrated in FIG. 7D, electrolytic plating (e.g., electrolytic copper plating) using the metal layer 102 as the plating power supplying layer is performed to form the through wiring 53 in the through hole 23. The protective film such as a resist film (not illustrated) covers and protects the upper surface of the metal layer 102 from the plating solution.

In the electrolytic plating process, a plating metal is gradually deposited and grown from a lower surface 102a of the metal layer 102 to fill the through hole 23. Thus, the gap between the metal layer 102 and the edge 20a of the substrate 20 (edge 32a of adhesive layer 32) is filled with the plating metal. Therefore, the through hole 23 is filled with the through wiring 53.

Figure 7E:
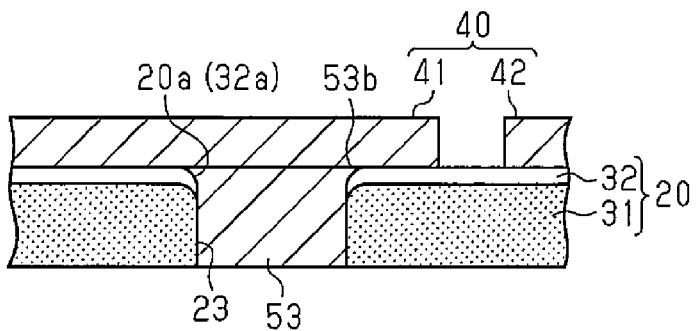

As illustrated in FIG. 7E, the metal layer 102 illustrated in FIG. 4A is patterned to form the wiring layer 40 (element mounting portions 41 and element connection portions 42).

In this manner, the element mounting portions 41 are formed from the metal layer 102 adhered to the base material 31 by the adhesive layer 32 (refer to FIG. 7C). Thus, the upper surface of each element mounting portions 41 is flat.

The through wiring 53 includes the plating metal that fills the gap between the metal layer 102 and the edge 20a of the substrate 20 (edge 32a of adhesive layer 32). Thus, the through wiring 53 includes the flange 53b that increases in diameter along the inner surface of the through hole 23 so that the upper surface of the flange 53b is flush with the upper surface of the substrate 20.

Next, the operation of the optical sensor 1 will now be described.

The optical sensor 1 includes the light emitting elements 71 and the light receiving element 74 mounted on the wiring substrate 10. The optical sensor 1 is attached to a measured object (e.g., human body surface) so that the upper side of the wiring substrate 10 on which the light emitting elements 71 and the light receiving element 74 are mounted, that is, the upper side of the optical sensor 1 contacts the measured object. The wiring substrate 10 is flexible. Therefore, the wiring substrate 10 is bent in accordance with the shape of the measured object. This brings the optical sensor 1 into close contact with the measured object.

The light emitting elements 71 are surrounded by the light shielding material 81, and the light receiving element 74 is surrounded by the light shielding material 83. When the wiring substrate 10 is bent, the angle between the light shielding materials 81, 83 is easily changed. Thus, the light shielding materials 81, 83 are brought into close contact with a rising part or a recessed part of the measured object. Therefore, it is difficult for light from the light emitting elements 71 to direct enter the light receiving element 74. Further, it is difficult for light from an object other than the measured object to enter the light receiving element 74. Thus, the light shielding materials 81, 83 restrict the noises, which are caused by the light directly incident from the light emitting elements 71 or by the light incident from other than the optical sensor 1 (light emitting elements 71), from being superimposed on signals (e.g., biological signals) obtained from the measured object.

The lower end faces of the through wirings 51, 52, 54, 55 exposed at the lower surface of the substrate 20 (lower surface of base material 31) respectively function as the external connection terminals P1a, P1b, P2a, P2b. The external connection terminals P1a, P1b, P2a, P2b are connected to wirings for using the optical sensor 1, that is, wirings for connecting the optical sensor 1 to a processing device that drives the light emitting elements 71 and processes the output signal of the light receiving element 74. The external connection terminals P1a, P1b, P2a, P2b are arranged on the surface (lower surface in FIG. 1B) of the wiring substrate 10 that is located opposite to the surface (upper surface in FIG. 1B) on which the light emitting elements 71 and the light receiving element 74 are arranged. Thus, connecting portions of the wirings that connect the optical sensor 1 to the processing device do not contact the measured object. Therefore, when the optical sensor 1 is attached to, for example, the human body surface, the user hardly feels uncomfortable due to the wiring.

As illustrated in FIG. 2, the substrate 20 includes the curved and rounded edge 31a, that is, "sag" extending in the stamping direction, in the upper surface of the base material 31 at the upper end portion of each through hole 23 covered by the wiring layer 40 (element mounting portion 41). The heat radiation through wiring 53 is formed in the through hole 23 of the substrate 20 by performing a given process (e.g., plating process or paste filling process) from the lower surface of the substrate 20. Thus, the heat radiation through wiring 53 includes the flange 53b that fills the gap between the edge 20a of the substrate 20 and the lower surface 40u of the wiring layer 40. The flange 53b limits the separation of the heat radiation through wiring 53 from the through hole 23 of the substrate 20. The through wirings 51, 52, 54, 55 illustrated in FIG. 1B are formed in the same manner as the through wirings 53. Thus, like the through wirings 53, the flanges of the through wirings 51, 52, 54, 55 limit the separation of the through wirings 51, 52, 54, 55 from the through holes 21, 22, 24, 25, respectively.

When the through wirings 53 are formed through electrolytic plating, the upper end portions of the through wirings 53 are bonded to the wiring layer 40 (element mounting portions 41). In contrast, the side surface 53a of each through wiring 53 is only in contact with the inner surface of the through hole 23. In the same manner, the through wirings 51, 52, 54, 55 formed through electrolytic plating are bonded to the wiring layer 40 (element mounting portions 41, element connection portions 42, element mounting portion 43, and element connection portion 44). In contrast, the side surface of each through wiring 51, 52, 54, 55 is only in contact with the inner surface of the corresponding through hole 21, 22, 24, 25. Therefore, when a force such as bending is applied to the substrate 20, the stress in the substrate 20 is hard to be transmitted to the side surfaces of the through wirings 51 to 55. Thus, the production of cracks in the through wirings 51 to 55 is limited.

The first embodiment has the advantages described below.

(1-1) The optical sensor 1 includes the light emitting elements 71 and light receiving element 74 mounted on the wiring substrate 10. The optical sensor 1 is attached to a measured object (e.g., human body surface) so that the upper side of the wiring substrate 10 on which the light emitting elements 71 and the light receiving element 74 are mounted, that is, the upper side of the optical sensor 1 contacts the measured object. The wiring substrate 10 is flexible. Therefore, the wiring substrate 10 is bent in accordance with the shape of the measured object. This brings the optical sensor 1 into close contact with the measured object.

(1-2) The light emitting elements 71 are surrounded by the light shielding material 81, and the light receiving element 74 is surrounded by the light shielding material 83. When the wiring substrate 10 is bent, the angle between the light shielding materials 81, 83 is easily changed. Thus, the light shielding materials 81, 83 are brought into close contact with a rising part or a recessed part of the measured object. Therefore, it is difficult for light from the light emitting elements 71 to direct enter the light receiving element 74. Further, it is difficult for light from an object other than the measured object to enter the light receiving element 74. Thus, the light shielding materials 81, 83 restrict the noises, which are caused by the light directly incident from the light emitting elements 71 or by the light incident from other than the optical sensor 1 (light emitting elements 71), from being superimposed on signals (e.g., biological signals) obtained from the measured object.

(1-3) The substrate 20 includes the curved and rounded edge 20a, that is, "sag" extending in the stamping direction, in the upper surface of the substrate 20 at the upper end portion of each through hole 23 covered by the wiring layer 40 (element mounting portion 41). Also, the substrate 20 includes the curved and rounded edges at the upper end portions of the through holes 21, 22, 24, 25 covered by the wiring layer 40 (element mounting portions 41, element connection portions 42, element mounting portion 43, and element connection portion 44). The through wirings 51 to 55 are formed in the through holes 21 to 25 of the substrate 20 by performing a given process (e.g., plating process or paste filling process) from the lower surface of the base material 31. This forms the flanges between the substrate 20 and the wiring layer 40 (element mounting portions 41, 43, element connection portions 42, 44). Thus, the flanges produce an anchor effect that limits the separation of the through wirings 51 to 55.

(1-4) When the through wirings 51 to 55 are formed through electrolytic plating, the upper end portions of the through wirings 51 to 55 are bonded to the wiring layer 40 (element mounting portions 41, element connection portions 42, element mounting portion 43, and element connection portion 44). In contrast, the side surface of each through wiring 51 to 55 is only in contact with the inner surface of the corresponding through hole 21 to 25. Therefore, when a force such as bending is applied to the substrate 20, the stress in the substrate 20 is hard to be transmitted to the side surfaces of the through wirings 51 to 55. Thus, the production of cracks in the through wirings 51 to 55 may be limited.

(1-5) The through holes 21 to 25 are formed extending through the base material 31 and the adhesive layer 32. The metal layer 102 is formed on the upper surface of the adhesive layer 32 to cover the through holes 21 to 25. The through holes 21 to 25 are filled with the plating metal through electrolytic plating using the metal layer 102 as a power supplying electrode. Consequently, the through wirings 51 to 55 are formed in the through holes 21 to 25. The plating metal is gradually deposited and grown from the lower surface 102a of the metal layer 102 to form the through wirings 51 to 55. Thus, the upper surfaces of the element mounting portions 41, 43 and the upper surfaces of the element connection portions 42, 44 are flat. Therefore, the light emitting elements 71 are reliably mounted on the element mounting portions 41, and the light receiving element 74 is reliably mounted on the element mounting portion 43. Further, the wires 73, 76 are reliably connected to the element connection portions 42, 44.

Second Embodiment

An optical sensor 1a according to a second embodiment will now be described. The same reference characters are given to elements of the second embodiment that are the same as the corresponding elements of the above first embodiment. Such elements will not be partially or entirely described.

As illustrated in FIGS. 8A and 8B, the optical sensor 1a includes a wiring substrate 10a, light emitting elements 71a, and the light receiving element 74. The light emitting elements 71a and the light receiving element 74 are mounted on the wiring substrate 10a.

The wiring substrate 10a includes the substrate 20, a wiring layer 40a, and the protective film 61. The wiring layer 40a and the protective film 61 are formed on one of the upper and lower surfaces of the substrate 20 (upper surface in FIG. 8A). The substrate 20 includes the base material 31 and the adhesive layer 32 formed on the upper surface of the base material 31.

The base material 31 is flexible and, for example, rectangular in a plan view. For example, a flexible film substrate using a resin, such as a polyimide or a polyester resin, or a liquid crystal polymer, or the like may be used as the base material 31. The base material 31 may have a thickness of, for example, 25 to 100 micrometer (μm). The adhesive layer 32 is formed on the upper surface of the base material 31 to adhere the wiring layer 40a to the base material 31. For example, an epoxy, polyimide, or silicone adhesive may be used as the material of the adhesive layer 32.

In the second embodiment, as illustrated in FIG. 8A, two light emitting elements 71a are mounted on the wiring substrate 10a. Each of the light emitting elements 71a includes two electrodes arranged on its upper surface. In the second embodiment, the wiring layer 40a includes two element mounting portions 41a, two element connection portions 42a, and two element connection portions 42b. Each of the light emitting elements 71a is mounted on one of the element mounting portions 41a and connected to one of the element connection portions 42a and one of the element connection portions 42b. Each element mounting portion 41a is located between the corresponding ones of the element connection portions 42a, 42b which are arranged at opposite sides of the element mounting portion 41a. For example, copper or a copper alloy may be used as the material of the wiring layer 40a.

For example, in the second embodiment, the two light emitting elements 71a each emit light having a different frequency. The light receiving element 74 has light receiving characteristics according to the light emitted from the two light emitting elements 71a. Each of the light emitting elements 71a may emit light having the same frequency.

As illustrated in FIG. 8B, the protective film 61 covers the upper surface of the adhesive layer 32. Further, the protective film 61 covers portions of the wiring layer 40a (portions of the element mounting portions 41a, 43 and portions of the element connection portions 42a, 42b, 44). The protective film 61 includes openings that partially expose the upper surfaces of the element mounting portions 41a, 43 and the upper surfaces of the element connection portions 42a, 42b, 44. A surface-processed layer (not illustrated) is formed on each of the exposed upper surfaces of the element mounting portions 41a, 43 and the element connection portions 42a, 42b, 44. Examples of the surface-processed layer include an Au layer, an Ni layer/Au layer (metal layer in which Ni layer is bottom layer and Au layer is formed on Ni layer), an Ni layer/Pd layer/Au layer (metal layer in which Ni layer, Pd layer, and Au layer are stacked in this order, with Ni layer serving as the bottom layer). Alternatively, the surface-processed layer may be formed by performing an anti-oxidation process such as an OSP process on the upper surface of the wiring layer 40a. When performing, for example, the OSP process, an organic coating such as that of an azole compound or an imidazole compound is formed as the surface-processed layer on the surface of the wiring layer 40a.

The through holes 21, 22 extending through the base material 31 and the adhesive layer 32 are formed in the substrate 20. The through holes 21 partially expose the lower surfaces of the element connection portions 42a and the through holes 22 partially expose the lower surfaces of the element connection portions 42b.

The through wirings 51, 52 are formed in the through holes 21, 22. The through wirings 51 are bonded to the element connection portions 42a and the through wirings 52 are bonded to the element connection portions 42b. Each of the through wirings 51, 52 includes the lower end face that is exposed at the lower surface of the substrate 20. The exposed lower end face of each through wiring 51 functions as the external connection terminal P1a and the exposed lower end face of each through wiring 52 functions as the external connection terminal P1b. For example, copper or a copper alloy may be used as the material of the through wirings 51, 52. The through wirings 51, 52 may be, for example, a plating metal (e.g., copper plating) formed in the through holes 21, 22 or a conductive paste (e.g., copper paste) with which the through holes 21, 22 are filled.

A surface-processed layer may be formed on the exposed lower end faces (external connection terminals P1a, P1b) of the through wirings 51, 52. For example, Au or an Au alloy, Ni or an Ni alloy, or Pd or a Pd alloy is used as the material of the surface-processed layer. Examples of the surface-processed layer include an Au layer, an Ni layer/Au layer, and an Ni layer/Pd layer/Au layer. Alternatively, the surface-processed layer may be formed by performing an anti-oxidation process such as an OSP process on the exposed lower end faces of the through wirings 51, 52. When the surface-processed layer is formed on the exposed lower end faces of the through wirings 51, 52, the surface-processed layer functions as external connection terminals.

The through holes 23 extending through the base material 31 and the adhesive layer 32 are also formed in the substrate 20. The through holes 23 are located immediately below the light emitting elements 71a. The through holes 23 partially expose the lower surfaces of the element mounting portions 41a. That is, as illustrated in FIG. 8A, the through holes 23 are arranged at locations overlapped with the light emitting elements 71a in a plan view.

The through wirings 53 are formed in the through holes 23. The through wirings 53 are bonded to the element mounting portions 41a. Each of the through wirings 53 includes the lower end face that is exposed at the lower surface of the substrate 20. The heat generated by each light emitting element 71a is transmitted through the corresponding element mounting portion 41a to the corresponding through wiring 53 located immediately below the light emitting element 71a. The heat transmitted to the through wirings 53 is then released from the exposed lower end faces of the through wirings 53. Thus, the exposed lower end faces of the through wirings 53 function as heat radiation surfaces that release the heat generated by the light emitting elements 71a mounted on the element mounting portions 41. That is, each of the through wirings 53 functions as a heat conductive member (heat radiation through wiring: thermal via) that releases the heat generated by the light emitting elements 71a. For example, copper or a copper alloy may be used as the material of the heat radiation through wirings 53. In the same manner as the through wirings 51, 52, a surface-processed layer may be formed on the exposed lower end faces of the heat radiation through wirings 53.

The through holes 24, 25 extending through the base material 31 and the adhesive layer 32 are also formed in the substrate 20. The through hole 24 partially exposes the lower surface of the element mounting portion 43 and the through hole 25 partially exposes the lower surface of the element connection portion 44. As illustrated in FIG. 8A, the through hole 24 is arranged at a location that is not overlapped with the light receiving element 74 mounted on the element mounting portion 43 in a plan view.

The through wirings 54, 55 are formed in the through holes 24, 25. The through wiring 54 is bonded to the element mounting portion 43 and the through wiring 55 is bonded to the element connection portion 44. Each of the through wirings 54, 55 includes the lower end face that is exposed at the lower surface of the substrate 20. The exposed lower end face of the through wiring 54 functions as the external connection terminal p2a and the exposed lower end face of the through wiring 55 functions as the external connection terminal P2b. For example, copper or a copper alloy may be used as the material of the through wirings 54, 55. In the same manner as the through wirings 51, 52, a surface-processed layer may be formed on the exposed lower end faces of the through wirings 54, 55.

The light emitting elements 71a are connected to the upper surfaces of the element mounting portions 41a by connection members 72a. The connection members 72a are formed from an adhesive having high thermal conductivity. For example, a member having high thermal conductivity, such as a thermal interface material (TIM), may be used as the connection members 72a. As the material of the thermal conductive member, for example, a soft metal, such as indium (In) or silver (Ag), a silicon gel, or an organic resin binder containing metal fillers, graphite or the like may be used.

One of the two electrodes arranged on the upper surface of each light emitting element 71a is connected to the corresponding element connection portion 42a by a wire 73a. The other one of the two electrodes is connected to the corresponding element connection portion 42b by a wire 73b. As the wires 73a, 73b, for example, an Au wire may be used.

The light receiving element 74 is connected to the upper surface of the element mounting portion 43 by the connection member 75. In the second embodiment, the light receiving element 74 includes electrodes that are arranged on the upper and lower surfaces of the light receiving element 74. As the connection member 75, an electrically conductive adhesive, for example, a silver paste may be used. The electrode arranged on the lower surface of the light receiving element 74 is connected to the element mounting portion 43 by the connection member 75. The electrode arranged on the upper surface of the light receiving element 74 is connected to the element connection portion 44 by the wire 76. As the wire 76, for example, an Au wire may be used.

The light shielding materials 81, 83 are arranged on the wiring substrate 10a. The light shielding materials 81, 83 are fixed to the upper surface of the protective film 61 of the wiring substrate 10a.

The light shielding material 81 is formed to have the shape of a rectangular frame and surrounds the light emitting elements 71a. An insulative resin that is colored with, for example, black may be used as the light shielding material 81. As the insulative resin, for example, an insulative resin, such as an epoxy resin or a polyimide resin, or a resin material in which filler such as silica or alumina is mixed into such an insulative resin may be used. Alternatively, the insulative resin may be, for example, an opaque black resist obtained by mixing a photosensitive material in an opaque black resin. A black pigment of carbon black, titanium black, or the like, or a mixture of multiple types of pigments may be used as a colorant mixed into the insulative resin.

The encapsulation resin 82 is formed within the region surrounded by the light shielding material 81 to encapsulate the light emitting elements 71a. The encapsulation resin 82 is light transmissive and transmits light according to the light emitting characteristics of the light emitting elements 71a. As the encapsulation resin 82, for example, a silicone resin may be used.

The light shielding material 83 is formed to have the shape of a rectangular frame and surrounds the light receiving element 74. The same material as the light shielding material 81 may be used as the light shielding material 83.

The encapsulation resin 84 is formed within the region surrounded by the light shielding material 83 to encapsulate the light receiving element 74. The encapsulation resin 84 is light transmissive and transmits light according to the light receiving characteristics of the light receiving element 74. As the encapsulation resin 84, for example, a silicone resin may be used.

Next, a process for mounting the elements on the wiring substrate 10a will now be described.

As illustrated in FIG. 9A, the wiring substrate 10a is prepared. The wiring layer 40a of the wiring substrate 10a includes the element mounting portions 41a, the element connection portions 42a, 42b, the element mounting portion 43, and the element connection portion 44. The wiring substrate 10a is formed by the same steps (refer to FIGS. 3A to 4C) as the wiring substrate 10 of the first embodiment.

As illustrated in FIG. 9B, the connection members 72a, 75 are formed on the upper surfaces of the element mounting portions 41a, 43. As the connection members 72a formed on the element mounting portions 41a, a member having high thermal conductivity, such as a thermal interface material (TIM), may be used. The connection members 72a are applied to the upper surfaces of the element mounting portions 41a by using, for example, a dispenser. As the connection member 75 formed on the element mounting portion 43, for example, a silver paste may be used. The connection member 75 is applied to the upper surface of the element mounting portion 43 by using, for example, a dispenser.

As illustrated in FIG. 9C, the light emitting elements 71a and the light receiving element 74 are mounted on the connection members 72a, 75, respectively, and the connection members 72a, 75 are cured by, for example, a thermal treatment. In the second embodiment, each of the light emitting elements 71a includes electrodes arranged on its upper surface. The light receiving element 74 includes electrodes arranged on its upper and lower surfaces. Through this step, the light emitting elements 71a are mechanically fixed to the element mounting portions 41a, and the light receiving element 74 is mechanically fixed to and electrically connected to the element mounting portion 43.

As illustrated in FIG. 9D, the light emitting elements 71a are connected to the element connection portions 42a, 42b by the wires 73a, 73b, and the light receiving element 74 is connected to the element connection portion 44 by the wire 76.

Figure 10A:
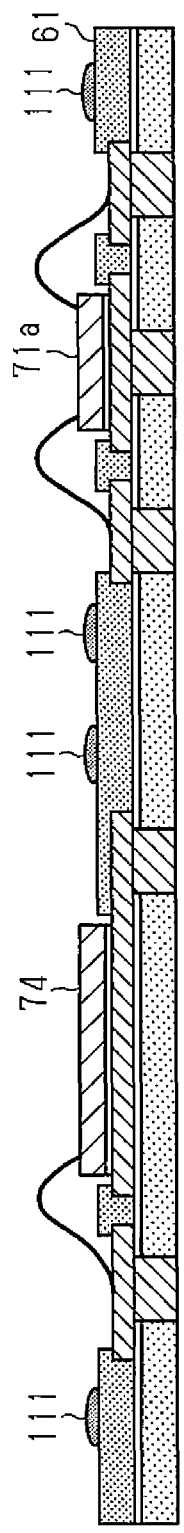

As illustrated in FIG. 10A, adhesives 111 are applied to the upper surface of the protective film 61. The adhesives 111 are arranged at positions of the light shielding materials 81, 83 illustrated in FIG. 8A and are formed to have the shape of a frame by, for example, using a dispenser. As the adhesives 111, for example, an epoxy adhesive may be used.

Figure 10B:
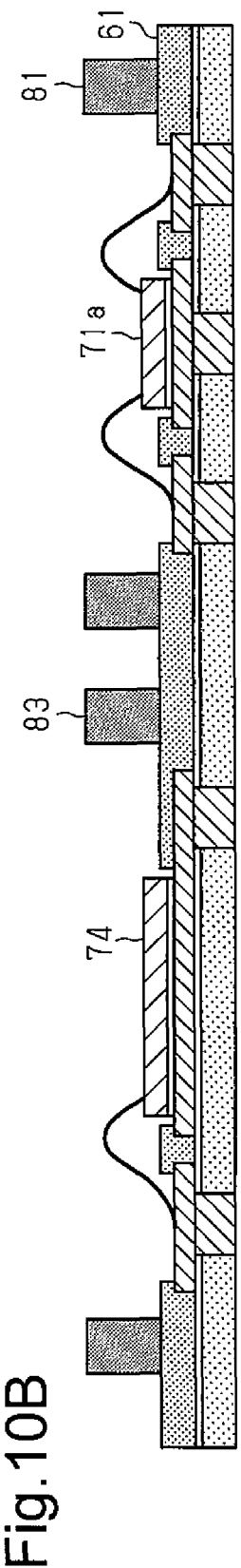

As illustrated in FIG. 10B, the light shielding materials 81, 83 are connected to the adhesives 111. The light shielding materials 81, 83 are obtained by, for example, arranging the light shielding materials 81, 83 formed from an insulative resin of a cured state on the upper surface of the protective layer 61 in a frame-shaped manner and thermally curing the adhesives 111 illustrated in FIG. 10A. In this manner, the light shielding materials 81, 83 are fixed to the upper surface of the protective film 61.

Figure 10C:
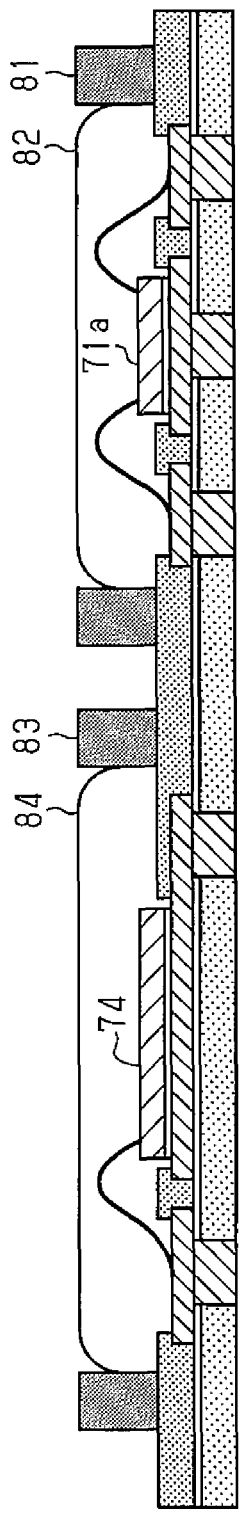

As illustrated in FIG. 10C, the region surrounded by the light shielding material 81 is filled with the encapsulation resin 82 to encapsulate the light emitting elements 71a. Also, the region surrounded by the light shielding material 83 is filled with the encapsulation resin 84 to encapsulate the light emitting element 74.

In addition to the advantages of the first embodiment, the second embodiment has the advantages described below.

(2-1) The optical sensor 1a including the light emitting elements 71a, which each have two electrodes on its upper surface, is obtained.

(2-2) By adjusting the material of the connection members 72a, which connect the light emitting elements 71a to the element mounting portions 41a, in accordance with the heat conductive property, a higher thermal conductivity may be obtained as compared when using the electrically conductive connection members. Thus, the heat generated by the light emitting elements 71a may be efficiently released.

(2-3) The light shielding materials 81, 83 are connected to the wiring substrate 10a by the adhesives 111. In this case, for example, the light shielding materials 81, 83 may be formed at the same time as when forming the wiring substrate 10a. This shortens the time for manufacturing the optical sensor 1a. Additionally, when the adhesives 111 are used, for example, a rubber, a metal, such as aluminum, or the like may be used as the light shielding materials 81, 83.

Third Embodiment

An optical sensor 1b according to a second embodiment will now be described. The same reference characters are given to elements of the third embodiment that are the same as the corresponding elements of the above first embodiment. Such elements will not be partially or entirely described.

As illustrated in FIGS. 11A and 11B, the optical sensor 1b includes a wiring substrate 10b, the light emitting elements 71, and the light receiving element 74. The light emitting elements 71 and the light receiving element 74 are mounted on the wiring substrate 10b.

The wiring substrate 10b includes the substrate 20, the wiring layer 40, and the protective film 61. The wiring layer 40 and the protective film 61 are formed on one of the upper and lower surfaces of the substrate 20 (upper surface in FIG. 11A). The substrate 20 includes the base material 31 and the adhesive layer 32 formed on the upper surface of the base material 31. The base material 31 is flexible and, for example, rectangular in a plan view. The wiring layer 40 is adhered to the base material 31 by the adhesive layer 32.

The wiring layer 40 includes the element mounting portions 41 on which the light emitting elements 71 are mounted and the element connection portions 42 connected to the light emitting elements 71. Further, the wiring layer 40 includes an element mounting portions 43a on which the light receiving element 74 is mounted and an element connection portion 44a connected to the light receiving element 74.

The through holes 21, 22 extending through the base material 31 and the adhesive layer 32 are formed in the substrate 20. The through wirings 51, 52 are formed in the through holes 21, 22. The through wirings 51 are bonded to the element mounting portions 41, and the through wirings 52 are bonded to the element connection portions 42.

The through holes 23 extending through the base material 31 and the adhesive layer 32 are also formed in the substrate 20. The through holes 23 are located immediately below the light emitting elements 71. The through holes 23 partially expose the lower surfaces of the element mounting portions 41 at locations where the light emitting elements 71 are mounted. That is, as illustrated in FIG. 11A, the through holes 23 are arranged at locations overlapped with the light emitting elements 71 in a plan view.

The through wirings 53 are formed in the through holes 23. The through wirings 53 are bonded to the element mounting portions 41. Each of the through wirings 53 includes the lower end face that is exposed at the lower surface of the substrate 20. The heat generated by each light emitting element 71 is transmitted through the corresponding element mounting portion 41 to the corresponding through wiring 53 located immediately below the light emitting element 71. The heat transmitted to the through wirings 53 is then released from the exposed lower end faces of the through wirings 53. Thus, the exposed lower end faces of the through wirings 53 function as heat radiation surfaces that release the heat generated by the light emitting elements 71 mounted on the element mounting portions 41. That is, each of the through wirings 53 functions as a heat conductive member (heat radiation through wiring: thermal via) that releases the heat generated by the light emitting elements 71. For example, copper or a copper alloy may be used as the material of the heat radiation through wirings 53. In the same manner as the through wirings 51, 52, a surface-processed layer may be formed on the exposed lower end faces of the heat radiation through wirings 53.

The through holes 24, 25 extending through the base material 31 and the adhesive layer 32 are also formed in the substrate 20. As illustrated in FIG. 11A, the through holes 24 are arranged in, for example, a matrix form in the element mounting portion 43a. Also, the through holes 25 are formed in the element connection portion 44a. In the third embodiment, the through holes 25 are arranged in a line in the element connection portion 44a.

The through wirings 54, 55 are formed in the through holes 24, 25. The through wirings 54 are bonded to the element mounting portion 43a and the through wirings 55 are bonded to the element connection portion 44a. Each of the through wirings 54, 55 includes the lower end face that is exposed at the lower surface of the substrate 20. The exposed lower end face of one of the through wirings 54 functions as the external connection terminal p2a and the exposed lower end face of one of the through wirings 55 functions as the external connection terminal P2b. For example, copper or a copper alloy may be used as the material of the through wirings 54, 55.

The light emitting elements 71 are connected to the upper surfaces of the element mounting portions 41 by the connection members 72. The connection members 72 are formed from an electrically conductive adhesive. The electrodes formed on the lower surfaces of the light emitting elements 71 are connected to the element mounting portions 41 by the connection members 72. Further, the light emitting elements 71 are connected to the element connection portions 42 by the wires 73.

The light receiving element 74 is connected to the upper surface of the element mounting portion 43a by the connection member 75. The connection member 75 is formed from an electrically conductive adhesive. The electrode formed on the lower surface of the light receiving element 74 is connected to the element mounting portions 43a by the connection member 75. Further, the light receiving element 74 is connected to the element connection portion 44a by the wire 76.

The light shielding material 81 is formed to have the shape of a rectangular frame and surrounds the light emitting elements 71. The encapsulation resin 82 is formed within the region surrounded by the light shielding material 81 to encapsulate the light emitting elements 71. The encapsulation resin 82 is light transmissive and transmits light according to the light emitting characteristics of the light emitting elements 71.

The light shielding material 83 is formed to have the shape of a rectangular frame and surrounds the light receiving element 74. The encapsulation resin 84 is formed within the region surrounded by the light shielding material 83 to encapsulate the light receiving element 74. The encapsulation resin 84 is light transmissive and transmits light according to the light receiving characteristics of the light receiving element 74.

In addition to the advantages of the first embodiment, the third embodiment has the advantages described below.

(3-1) The wiring substrate 10b includes the through wirings 54 that are formed in the through holes 24 extending through the substrate 20 (base material 31 and adhesive layer 32). The through wirings 54 are bonded to the element mounting portion 43*a*. The through wirings 54 increase the rigidity of the portion where the element mounting portion 43*a* is formed. Also, the through wirings 55 are bonded to the element connection portion 44*a*. The through wirings 55 increase the rigidity of the portion where the element connection portion 44*a* is formed. According to this structure, when mounting the light receiving element 74 on the element mounting portion 43*a* or when connecting the wire 76 to the element connection portion 44*a*, the force applied by a connection apparatus (die bonder or wire bonder) may be received by the element mounting portion 43*a* or the element connection portion 44*a*. Thus, the through wirings 54 and 55 allow for easy mounting of the elements (in this embodiment, light receiving element 74).

Fourth Embodiment

An optical sensor 1*c* according to a fourth embodiment will now be described. The same reference characters are given to elements of the fourth embodiment that are the same as the corresponding elements of the above first embodiment. Such elements will not be partially or entirely described.

As illustrated in FIGS. 12A and 12B, the optical sensor 1*c* includes a wiring substrate 10*c*, the light emitting elements 71, and the light receiving element 74. The light emitting elements 71 and the light receiving element 74 are mounted on the wiring substrate 10*c*.

The wiring substrate 10*c* includes the substrate 20, the wiring layer 40, and the protective film 61. The wiring layer 40 and the protective film 61 are formed on one of the upper and lower surfaces of the substrate 20 (upper surface in FIG. 12A). The substrate 20 includes the base material 31 and the adhesive layer 32 formed on the upper surface of the base material 31. The base material 31 is flexible and, for example, rectangular in a plan view. The wiring layer 40 is adhered to the base material 31 by the adhesive layer 32.

The wiring layer 40 includes the element mounting portions 41 on which the light emitting elements 71 are mounted and the element connection portions 42 connected to the light emitting elements 71. Further, the wiring layer 40 includes the element mounting portion 43 on which the light receiving element 74 is mounted and the element connection portion 44 connected to the light receiving element 74.

The through holes 21, 22 extending through the base material 31 and the adhesive layer 32 are formed in the substrate 20. The through wirings 51, 52 are formed in the through holes 21, 22. The through wirings 51 are bonded to the element mounting portions 41, and the through wirings 52 are bonded to the element connection portions 42.

The through holes 23 extending through the base material 31 and the adhesive layer 32 are also formed in the substrate 20. The through holes 23 are located immediately below the light emitting elements 71. The heat radiation through wirings 53 (thermal vias) are formed in the through holes 23. The heat radiation through wirings 53 are bonded to the element mounting portions 41.

The through holes 24, 25 extending through the base material 31 and the adhesive layer 32 are also formed in the substrate 20. The through wirings 54, 55 are formed in the through holes 24, 25. The through wiring 54 is bonded to the element mounting portion 43 and the through wiring 55 is bonded to the element connection portion 44.

The light shielding material 81 is formed to have the shape of a rectangular frame and surrounds the light emitting elements 71. The encapsulation resin 82 is formed within the region surrounded by the light shielding material 81 to encapsulate the light emitting elements 71. The encapsulation resin 82 is light transmissive and transmits light according to the light emitting characteristics of the light emitting elements 71.

The light shielding material 83 is formed to have the shape of a rectangular frame and surrounds the light receiving element 74. The encapsulation resin 84 is formed within the region surrounded by the light shielding material 83 to encapsulate the light receiving element 74. The encapsulation resin 84 is light transmissive and transmits light according to the light receiving characteristics of the light receiving element 74.

In the fourth embodiment, through holes 26*a*, 26*b* are formed in the wiring substrate 10*c* outside the light shielding materials 81, 83. As illustrated in FIG. 12B, the through holes 26*a*, 26*b* extend through the base material 31 and the adhesive layer 32 of the substrate 20 and the protective film 61.

As illustrated in FIG. 12A, the through holes 26*a* are located between the light shielding materials 81, 83 and extend along the light shielding materials 81, 83 in the width direction of the wiring substrate 10*c* (the vertical direction in FIG. 12A). The through holes 26*b* are located at and extend along the peripheral edge of the wiring substrate 10*c*.

In addition to the advantages of the first embodiment, the fourth embodiment has the advantages described below.

(4-1) The wiring substrate 10*c* includes the through holes 26*a*, 26*b* that are formed outside the light shielding materials 81, 83 and extend through the base material 31 and the adhesive layer 32 of the substrate 20 and the protective film 61. The through holes 26*a*, 26*b* allow for easy deformation (bending) of the wiring substrate 10*c*. This brings the optical sensor 1*c* into close contact with the measured object.

It should be apparent to those skilled in the art that the foregoing embodiments may be employed in many other specific forms without departing from the scope of this disclosure. Particularly, it should be understood that the foregoing embodiments may be employed in the following forms.

In the above embodiments, the shape of each through wiring exposed at the lower surface of the substrate 20 may be appropriately changed.

Figure 13:
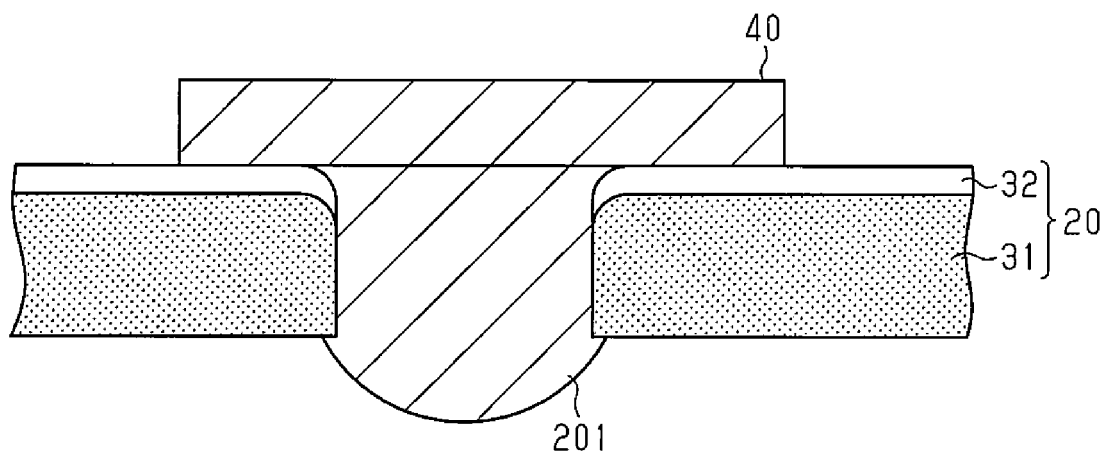
FIGS. 13, 14, 15, and 16A are schematic cross-sectional views partially illustrating various modified examples of an optical sensor.

As illustrated in FIG. 13, a through wiring 201 includes a lower portion that protrudes from the lower surface of the substrate 20 (base material 31). The lower portion of the through wiring 201 protruding from the lower surface of the substrate 20 (base material 31) has an arcuate cross-section. In the same manner as the above embodiments, a surface-processed layer may be formed on the surface of the protruded lower portion of the through wiring 201.

Figure 14:
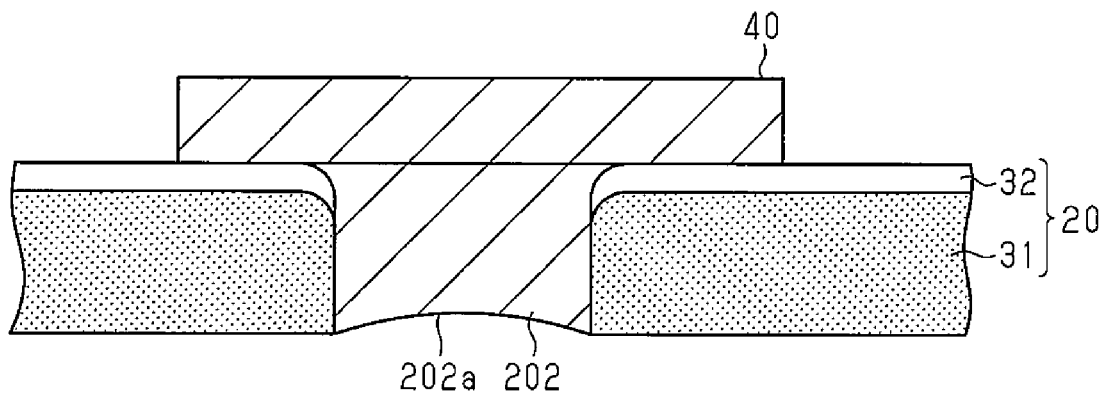

As illustrated in FIG. 14, a through wiring 202 includes a lower surface 202*a* that is recessed such that the center portion of the lower surface 202*a* is located at an upper position (i.e., near the center of the base material 31) than the circumference portion of the lower surface 202*a*.

The shape of each of the through wirings 201, 202 increases the area of the lower end face of the through wiring exposed at the lower surface of the base material 31 as compared when the lower end face of each through wiring is flat. Therefore, when each of the through wirings 201, 202 is connected to an external wiring, the area of the through wiring that contacts the external wiring is increased. This ensures the connection of each through wiring to the external wiring.

In the above embodiments, the location and the shape of the through wirings may be appropriately changed.

Figure 15:
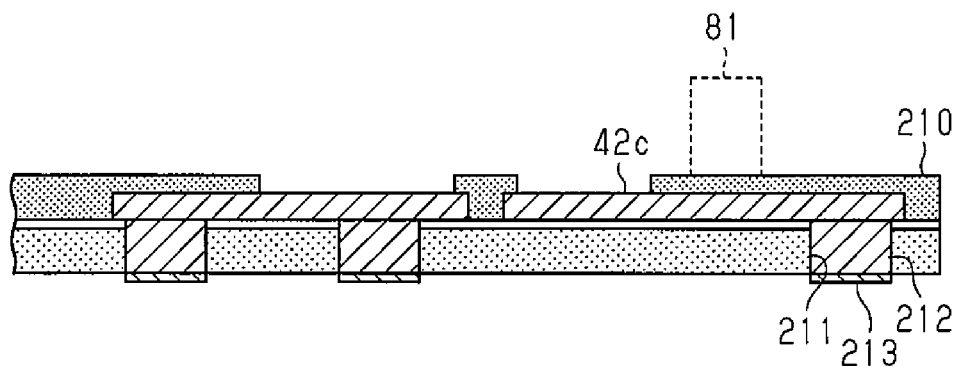

As illustrated in FIG. 15, a wiring substrate 210 includes an element connection portion 42c that extends outward toward the end of the wiring substrate 210 than the light shielding material 81 illustrated by broken lines in FIG. 15. Also, the wiring substrate 210 includes a through hole 211 that is formed outside the light shielding material 81 (right side in FIG. 15). A through wiring 212 is formed in the through hole 211. In FIG. 15, a surface-processed layer 213 is formed on the lower end face of each of the through wirings including the through wiring 212.

Figure 16A:
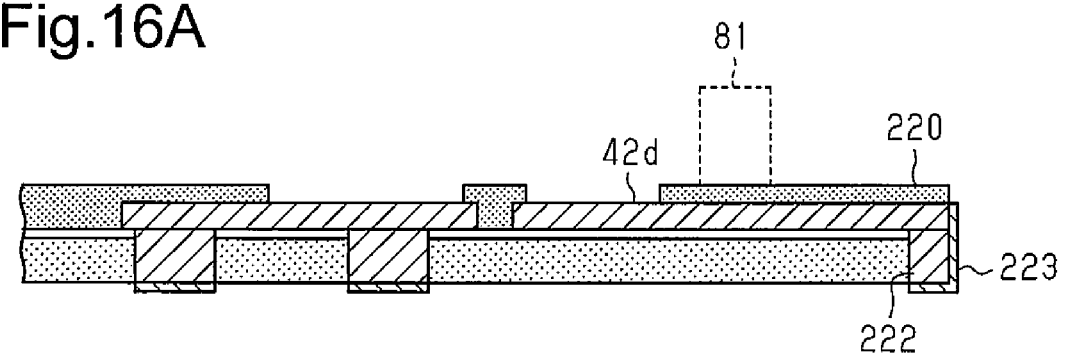

As illustrated in FIG. 16A, a wiring substrate 220 includes an element connection portion 42d that extends to the end of the wiring substrate 220. A through wiring 222 is formed at the end of the wiring substrate 220. A surface-processed layer 223 is formed on the lower end face of each of the through wirings including the through wiring 222. Additionally, the surface-processed layer 223 is formed on the side surface of the through wiring 222 and the side surface of the element connection portion 42d that are exposed from the end of the wiring substrate 220.

Figure 16B:
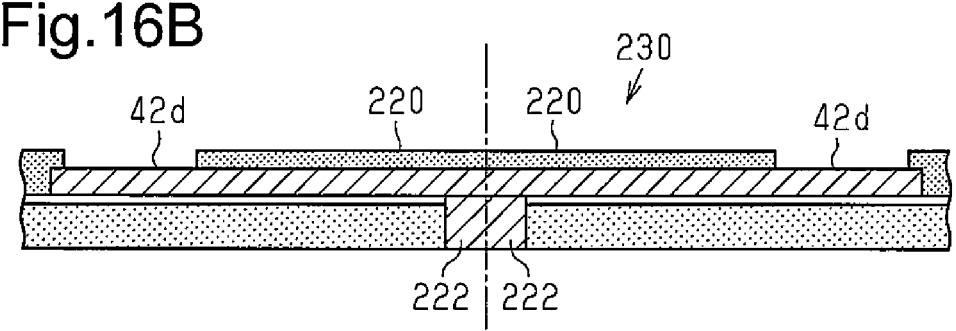
FIG. 16B is a schematic cross-sectional view illustrating a method for manufacturing the optical sensor illustrated in FIG. 16A.

As illustrated in FIG. 16B, the through wiring 222 is obtained by cutting a substrate 230 along a cutting line illustrated by single-dashed lines in FIG. 16B and singulating the substrate 230 into a plurality of (here, two) wiring substrates 220. That is, after manufacturing a batch of the wiring substrates 220 on one substrate 230, the substrate 230 is singulated into individual wiring substrates 220.

In the above embodiments, each of the through wirings 51 to 55 has the shape of a circle (e.g., refer to FIG. 1A) in a plan view, but may have a rectangular shape or a polygonal shape in a plan view.

In the above embodiments, each of the light shielding materials 81, 83 has the shape of a rectangular frame (e.g., refer to FIG. 1A) in a plan view, but may have the shape of a circle or a polygonal frame in a plan view.

In the above embodiments, each of the wiring substrates 10, 10a, 10b, 10c is rectangular (e.g., refer to FIG. 1A) in a plan view, but may be circular or polygonal in a plan view.

In the above embodiments, in the same manner as the light emitting elements 71a of the second embodiment, the light receiving element may include two electrodes on its upper surface. In this case, in the same manner as the element connection portions 42a, 42b of the second embodiment, two element connection portions that are connected to the light receiving element are formed.

Clauses

This disclosure further encompasses the following embodiments.

1. A method for manufacturing an optical sensor, the method including:
forming a plurality of through holes in a flexible substrate;
arranging a metal layer on an upper surface of the substrate to cover the through holes;
forming a plurality of through wirings in the through holes;
patterning the metal layer to form a plurality of element mounting portions and a plurality of element connection portions;
mounting a light emitting element and a light receiving element on the element mounting portions, respectively;
connecting the light emitting element and the light receiving element to the element connection portions by wires, respectively;
forming a plurality of light shielding materials to respectively surround the light emitting element and the light receiving element; and
forming a plurality of encapsulation resins to respectively encapsulate the light emitting element and the light receiving element,
wherein the through wirings include a heat radiation through wiring that is formed immediately below the light emitting element and bonded to the element mounting portion on which the light emitting element is mounted.

2. The method according to clause 1, wherein the forming a plurality of through holes includes performing a stamping process from the upper surface of the substrate to form the through holes, wherein the stamping process causes a plurality of rounded edges to be formed in the upper surface of the substrate at upper end portions of the through holes, and
the forming a plurality of through wirings includes forming each of the through wirings to have a flange between a corresponding one of the rounded edges of the substrate and a corresponding one of the element mounting portions and the element connection portions.

3. The method according to clause 1 or 2, wherein the through wirings are formed through electrolytic plating by using the metal layer as a power supplying electrode.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to an illustration of the superiority and inferiority of the invention. Although embodiments have been described in detail, it should be understood that various changes, substitutions, and alterations could be made hereto without departing from the scope of this disclosure.

The invention claimed is:

1. An optical sensor comprising:
a flexible substrate;
a light emitting element;
a light receiving element;
a plurality of element mounting portions formed on an upper surface of the substrate, wherein each of the light emitting element and the light receiving element is mounted on one of the element mounting portions;
a plurality of element connection portions formed on the upper surface of the substrate, wherein each of the element connection portions is connected to one of the light emitting element and the light receiving element by a wire;
a plurality of through wirings respectively formed in a plurality of through holes extending through the substrate, wherein
each of the through wirings is bonded to one of the element mounting portions or one of the element connection portions, and
the through wirings include a heat radiation through wiring that is located immediately below the light emitting element and bonded to the element mounting portion on which the light emitting element is mounted;
a plurality of light shielding materials that are each frame-shaped, wherein each of the light emitting element and the light receiving element is surrounded by one of the light shielding materials; and
a plurality of encapsulation resins each arranged within a region surrounded by one of the light shielding materials, wherein each of the light emitting element and the light receiving element is encapsulated by one of the encapsulation resins.

2. The optical sensor according to claim 1, wherein
the substrate includes rounded edges, wherein each of the rounded edges is formed in the upper surface of the substrate at an upper end portion of each through hole covered by the one of the element mounting portions or one of the element connection portions, and
each of the through wirings includes a flange that is formed between one of the rounded edges of the substrate and the corresponding element mounting portion or element connection portion.

3. The optical sensor according to claim 1, wherein
the light emitting element includes an upper surface on which a plurality of electrodes are arranged,
the optical sensor further comprises a connection member that thermally connects the light emitting element to the element mounting portion on which the light emitting element is mounted, and
the light emitting element is connected to two or more of the element connection portions by a plurality of wires corresponding to the number of the electrodes of the light emitting element.

4. The optical sensor according to claim 1, wherein
the substrate includes a plurality of through holes that are formed outside the light shielding materials.

5. The optical sensor according to claim 1, wherein
two or more of the through wirings are bonded to the element mounting portion on which the light receiving element is mounted.

6. The optical sensor according to claim 1, wherein
two or more of the through wirings are bonded to the element connection portion connected to the light receiving element.

7. The optical sensor according to claim 1,
the light emitting element is one of a plurality of light emitting element that are arranged within the region surrounded by the corresponding one of the light shielding materials.

\* \* \* \* \*